United States Patent [19]
Williams et al.

[11] Patent Number: 5,437,863
[45] Date of Patent: Aug. 1, 1995

[54] METHOD OF ENHANCING THE GROWTH OF GUT EPITHELIAL CELLS BY ADMINISTRATION OF A CYTOKINE SUCH AS INTERLEUKIN II

[75] Inventors: David A. Williams, Indianapolis, Ind.; Steven C. Clark, Winchester, Mass.

[73] Assignee: Genetics Institute, Inc., Cambridge, Mass.

[21] Appl. No.: 115,680

[22] Filed: Sep. 1, 1993

Related U.S. Application Data

[63] Continuation-in-part of Ser. No. 941,372, Sep. 2, 1992.

[51] Int. Cl.$^6$ ............... A61K 38/18; A61K 38/19; A61K 38/20
[52] U.S. Cl. ............................ 424/85.1; 424/85.2
[58] Field of Search ............... 514/2, 21, 880, 893, 514/925; 424/85.1, 85.2

[56] References Cited

U.S. PATENT DOCUMENTS

| | | | |
|---|---|---|---|
| 5,082,658 | 1/1992 | Palladino | 424/85.2 |
| 5,214,066 | 5/1993 | Szabo | 514/423 |
| 5,215,895 | 6/1993 | Bennett et al. | 435/69.52 |
| 5,262,319 | 11/1993 | Iwata et al. | 435/240.2 |

FOREIGN PATENT DOCUMENTS

WO91/07495  5/1991  WIPO .

OTHER PUBLICATIONS

Wu et al., Radiation Res. 123: 112–115 ('90).
Du et al., Blood 83(1): 33–37 ('94).
Wilmore et al., Surgery 104(5): 917–923 ('88).
Steadman's Medical Dictionary, 25th Ed., Williams and Wilkins, Baltimore, Md., 1990, pp. 34–35, 395–396.
F. Takatsuki et al, "Interleukin 6 Perfusion Stimulates Reconstitution of the Immune and Hematopoietic Systems after 5-Fluorouracil Treatment", Cancer Research, 50:2885–2890 (May 15, 1990).
D. P. Gearing et al, "the IL–6 Signal Transducer, gp130: An Oncostatin M Receptor and Affinity Converter for the LIF Receptor", Science, 255:1434–1437 (Mar. 13, 1992).
N. Y. Ip et al, "CNTF and LIF Act on Neuronal Cells via Shared Signaling Pathways that Involve the IL–6 Signal Transducing Receptor Component gp130", Cell, 69:1121–1132 (Jun. 26, 1992).
G. Damia et al, "Prevention of Acute Chemotherapy-induced Death in Mice by Recombinant Human Interleukin 1: Protection from Hematological and Nonhematological Toxicities", Cancer Research, 52:4082–4089 (Aug. 1, 1992).
K. M. Zsebo et al, "Radioprotection of Mice by Recombinant Rat Stem Cell Factor", Proc. Natl. Acad. Sci. USA, 89:9464–9468 (Oct. 1992).
R. Neta et al, "The in vivo Effects of Interleukin 1: Bone Marrow Cells are Induced to Cycle after Administration of Interleukin 1", J. Immunol., 139(6):1861–1866 (Sep. 15, 1987) [Neta I].
R. Neta et al, "Interleukin 1 is a Radioprotector", J. Immunol., 136(7):2483–2485 (Apr. 1, 1986) [Neta II].
J. L. Gabrilove et al, "Effect of Granulocyte Colony-Stimulating Factor on Nuetropenia and Associated Morbidity due to Chemotherapy for Transitional-Cell Carcinoma of the Urothelium", The new England Journal of Medicine, 318(22):1414–1422 (Jun. 2, 1988).

(List continued on next page.)

Primary Examiner—Robert A. Wax
Assistant Examiner—Eric Grimes
Attorney, Agent, or Firm—M. C. Meinert; Thomas J. DesRosier; Mary E. Bak

[57] ABSTRACT

A method of restoring damaged or depleted cell populations by treating the patient with cytokines, particularly IL-11 and IL-6.

27 Claims, 9 Drawing Sheets

OTHER PUBLICATIONS

S. Vadhan-Raj et al, "Abrogating Chemotherapy-Induced Myelosuppression by Recombinant Granulocyte-Macrophage Colony-Stimulating Factor in Patients with Sarcoma: Protection at the Progenitor Cell Level", J. Clin. Oncology, 10(8):1266-1277 (Aug. 1992).

X. Du et al, "Effects of Recombinant Human Interleukin-11 on Hematopoietic Reconstitution in Transplant Mice: Acceleration of Recovery of Peripheral Blood Neutrophils and Platelets", Blood, 81(1):27-34 (Jan. 1, 1993).

S. Paul et al, "Molecular Cloning of a cDNA Encoding Interleukin 11, a Stromal Cell-Derived Lymphopoietic and Hematopoietic Cytokine", Proc. Natl. Acad. Sci. USA, 87:7512-7516 (Oct. 1990).

F. Balkwill et al, "The Cytokine Network", Immunology Today, 10(9):299-304 (1989).

S. Clark et al, "The Human Hematopoietic Colony-Stimulating Factors", Science, 236:1229-1237 (Jun. 5, 1987).

FIGURE 1

Human IL-11 nucleotide sequence [SEQ ID NO: 1]
and amino acid sequence [SEQ ID NO: 2]

5'AGCTGGGAAGGGTTAAAGGCCCCCGGCTCCCTGCCCCCTGCCCTGG

```
                                  (1)
GGAACCCCT GGCCCTGCGGGGA ATG AAC TGT GTT TGC CGC
                         M   N   C   V   C   R

CTG GTC CTG GTC GTG CTG AGC CTG TGG CCA GAT ACA
 L   V   L   V   V   L   S   L   W   P   D   T

GCT GTC GCC CCT GGG CCA CCA CCT GGC CCC CCT CGA
 A   V   A   P   G   P   P   P   G   P   P   R

GTT TCC CCA GAC CCT CGG GCC GAG CTG GAC AGC ACC
 V   S   P   D   P   R   A   E   L   D   S   T

GTG CTC CTG ACC CGC TCT CTC CTG GCG GAC ACG CGG
 V   L   L   T   R   S   L   L   A   D   T   R

CAG CTG GCT GCA CAG CTG AGG GAC AAA TTC CCA GCT
 Q   L   A   A   Q   L   R   D   K   F   P   A

GAC GGG GAC CAC AAC CTG GAT TCC CTG CCC ACC CTG
 D   G   D   H   N   L   D   S   L   P   T   L

GCC ATG AGT GCG GGG GCA CTG GGA GCT CTA CAG CTC
 A   M   S   A   G   A   L   G   A   L   Q   L

CCA GGT GTG CTG ACA AGG CTG CGA GCG GAC CTA CTG
 P   G   V   L   T   R   L   R   A   D   L   L

TCC TAC CTG CGG CAC GTG CAG TGG CTG CGC CGG GCA
 S   Y   L   R   H   V   Q   W   L   R   R   A

GGT GGC TCT TCC CTG AAG ACC CTG GAG CCC GAG CTG
 G   G   S   S   L   K   T   L   E   P   E   L

GGC ACC CTG CAG GCC CGA CTG GAC CGG CTG CTG CGC
 G   T   L   Q   A   R   L   D   R   L   L   R

CGG CTG CAG CTC CTG ATG TCC CGC CTG GCC CTG CCC
 R   L   Q   L   L   M   S   R   L   A   L   P

CAG CCA CCC CCG GAC CCG CCG GCC CCC CCG CTG GCG
 Q   P   P   P   D   P   P   A   P   P   L   A

CCC CCC TCC TCA GCC TGG GGG GGC ATC AGG GCC GCC
 P   P   S   S   A   W   G   G   I   R   A   A
```

FIGURE 1A

```
CAC GCC ATC CTG GGG GGG CTG CAC CTG ACA CTT GAC
 H   A   I   L   G   G   L   H   L   T   L   D

TGG GCC GTG AGG GGA CTG CTG CTG CTG AAG ACT CGG
 W   A   V   R   G   L   L   L   L   K   T   R

CTG TGA CCCGAGGCCCAGAGCCACCACCGTCCTTCCAAAGCCACA
 L
```

TCTTATTTATTTATTTATTTCGGTACTGGGGGCGAAACAGCCAGGTG

ATCCCCCTGCCTTTAGCTCCCCCTAGTTAGAGACAGTCCTTCCGTGA

GGCTGGGGGGCATCTGTGCCTTATTTATACTTATTTATTTCAGGAGC

GGGGGTGGGCTCCTGGGTCCCCGAGGAGGAGGGAGCTGGGGTCCCGG

ATTCTTGTGTCCACAGACTTCTGCCCTGGCTCCTCCCCCTCGAGGCC

TGGGCAGGAATACATACTATTTATTTAAGAGCTC

FIGURE 2 pALtrxA/EK/IL-11ΔPro-581
SEQ ID NO:3 and SEQ ID NO:4

```
GACGAAAGGG CCTCGTGATA CGCCTATTTT TATAGGTTAA   40
TGTCATGATA ATAATGGTTT CTTAGACGTC AGGTGGCACT   80
TTTCGGGGAA ATGTGCGCGG AACCCCTATT TGTTTATTTT  120
TCTAAATACA TTCAAATATG TATCCGCTCA TGAGACAATA  160
ACCCTGATAA ATGCTTCAAT AATATTGAAA AAGGAAGAGT  200
ATGAGTATTC AACATTTCCG TGTCGCCCTT ATTCCCTTTT  240
TTGCGGCATT TTGCCTTCCT GTTTTGCTC ACCCAGAAAC   280
GCTGGTGAAA GTAAAAGATG CTGAAGATCA GTTGGGTGCA  320
CGAGTGGGTT ACATCGAACT GGATCTCAAC AGCGGTAAGA  360
TCCTTGAGAG TTTTCGCCCC GAAGAACGTT TTCCAATGAT  400
GAGCACTTTT AAAGTTCTGC TATGTGGCGC GGTATTATCC  440
CGTATTGACG CCGGGCAAGA GCAACTCGGT CGCCGCATAC  480
ACTATTCTCA GAATGACTTG GTTGAGTACT CACCAGTCAC  520
AGAAAAGCAT CTTACGGATG GCATGACAGT AAGAGAATTA  560
TGCAGTGCTG CCATAACCAT GAGTGATAAC ACTGCGGCCA  600
ACTTACTTCT GACAACGATC GGAGGACCGA AGGAGCTAAC  640
CGCTTTTTTG CACAACATGG GGATCATGT AACTCGCCTT   680
GATCGTTGGG AACCGGAGCT GAATGAAGCC ATACCAAACG  720
ACGAGCGTGA CACCACGATG CCTGTAGCAA TGGCAACAAC  760
GTTGCGCAAA CTATTAACTG GCGAACTACT TACTCTAGCT  800
TCCCGGCAAC AATTAATAGA CTGGATGGAG GCGGATAAAG  840
TTGCAGGACC ACTTCTGCGC TCGGCCCTTC CGGCTGGCTG  880
GTTTATTGCT GATAAATCTG GAGCCGGTGA GCGTGGGTCT  920
CGCGGTATCA TTGCAGCACT GGGGCCAGAT GGTAAGCCCT  960
CCCGTATCGT AGTTATCTAC ACGACGGGGA GTCAGGCAAC 1000
TATGGATGAA CGAAATAGAC AGATCGCTGA GATAGGTGCC 1040
```

FIGURE 2A

TCACTGATTA AGCATTGGTA ACTGTCAGAC CAAGTTTACT 1080

CATATATACT TTAGATTGAT TTAAAACTTC ATTTTTAATT 1120

TAAAAGGATC TAGGTGAAGA TCCTTTTTGA TAATCTCATG 1160

ACCAAAATCC CTTAACGTGA GTTTTCGTTC CACTGAGCGT 1200

CAGACCCCGT AGAAAAGATC AAAGGATCTT CTTGAGATCC 1240

TTTTTTTCTG CGCGTAATCT GCTGCTTGCA AACAAAAAAA 1280

CCACCGCTAC CAGCGGTGGT TTGTTTGCCG GATCAAGAGC 1320

TACCAACTCT TTTTCCGAAG GTAACTGGCT TCAGCAGAGC 1360

GCAGATACCA AATACTGTCC TTCTAGTGTA GCCGTAGTTA 1400

GGCCACCACT TCAAGAACTC TGTAGCACCG CCTACATACC 1440

TCGCTCTGCT AATCCTGTTA CCAGTGGCTG CTGCCAGTGG 1480

CGATAAGTCG TGTCTTACCG GGTTGGACTC AAGACGATAG 1520

TTACCGGATA AGGCGCAGCG GTCGGGCTGA ACGGGGGGTT 1560

CGTGCACACA GCCCAGCTTG GAGCGAACGA CCTACACCGA 1600

ACTGAGATAC CTACAGCGTG AGCATTGAGA AAGCGCCACG 1640

CTTCCCGAAG GGAGAAAGGC GGACAGGTAT CCGGTAAGCG 1680

GCAGGGTCGG AACAGGAGAG CGCACGAGGG AGCTTCCAGG 1720

GGGAAACGCC TGGTATCTTT ATAGTCCTGT CGGGTTTCGC 1760

CACCTCTGAC TTGAGCGTCG ATTTTGTGA TGCTCGTCAG 1800

GGGGGCGGAG CCTATGGAAA AACGCCAGCA ACGCGGCCTT 1840

TTTACGGTTC CTGGCCTTTT GCTGGCCTTT TGCTCACATG 1880

TTCTTTCCTG CGTTATCCCC TGATTCTGTG ATAACCGTA 1920

TTACCGCCTT TGAGTGAGCT GATACCGCTC GCCGCAGCCG 1960

AACGACCGAG CGCAGCGAGT CAGTGAGCGA GGAAGCGGAA 2000

GAGCGCCCAA TACGCAAACC GCCTCTCCCC GCGCGTTGGC 2040

CGATTCATTA ATGCAGAATT GATCTCTCAC CTACCAAACA 2080

ATGCCCCCCT GCAAAAAATA AATTCATATA AAAACATAC 2120

AGATAACCAT CTGCGGTGAT AAATTATCTC TGGCGGTGTT 2160

FIGURE 2B

GACATAAATA CCACTGGCGG TGATACTGAG CACATCAGCA 2200

GGACGCACTG ACGACCATGA ATTCAAGAAG GAGATATACA 2240

| T | ATG | AGC | GAT | AAA | ATT | ATT | CAC | CTG | ACT | GAC | GAC | 2274 |
|---|---|---|---|---|---|---|---|---|---|---|---|---|
| | Met | Ser | Asp | Lys | Ile | Ile | His | Leu | Thr | Asp | Asp | |
| | 1 | | | | 5 | | | | | 10 | | |

| AGT | TTT | GAC | ACG | GAT | GTA | CTC | AAA | GCG | GAC | GGG | 2307 |
|---|---|---|---|---|---|---|---|---|---|---|---|
| Ser | Phe | Asp | Thr | Asp | Val | Leu | Lys | Ala | Asp | Gly | |
| | | | 15 | | | | | 20 | | | |

| GCG | ATC | CTC | GTC | GAT | TTC | TGG | GCA | GAG | TGG | TGC | 2340 |
|---|---|---|---|---|---|---|---|---|---|---|---|
| Ala | Ile | Leu | Val | Asp | Phe | Trp | Ala | Glu | Trp | Cys | |
| | | 25 | | | | | 30 | | | | |

| GGT | CCG | TGC | AAA | ATG | ATC | GCC | CCG | ATT | CTG | GAT | 2373 |
|---|---|---|---|---|---|---|---|---|---|---|---|
| Gly | Pro | Cys | Lys | Met | Ile | Ala | Pro | Ile | Leu | Asp | |
| | 35 | | | | | 40 | | | | | |

| GAA | ATC | GCT | GAC | GAA | TAT | CAG | GGC | AAA | CTG | ACC | 2406 |
|---|---|---|---|---|---|---|---|---|---|---|---|
| Glu | Ile | Ala | Asp | Glu | Tyr | Gln | Gly | Lys | Leu | Thr | |
| 45 | | | | | 50 | | | | | 55 | |

| GTT | GCA | AAA | CTG | AAC | ATC | GAT | CAA | AAC | CCT | GGC | 2439 |
|---|---|---|---|---|---|---|---|---|---|---|---|
| Val | Ala | Lys | Leu | Asn | Ile | Asp | Gln | Asn | Pro | Gly | |
| | | | | 60 | | | | | 65 | | |

| ACT | GCG | CCG | AAA | TAT | GGC | ATC | CGT | GGT | ATC | CCG | 2472 |
|---|---|---|---|---|---|---|---|---|---|---|---|
| Thr | Ala | Pro | Lys | Tyr | Gly | Ile | Arg | Gly | Ile | Pro | |
| | | | 70 | | | | | 75 | | | |

| ACT | CTG | CTG | CTG | TTC | AAA | AAC | GGT | GAA | GTG | GCG | 2505 |
|---|---|---|---|---|---|---|---|---|---|---|---|
| Thr | Leu | Leu | Leu | Phe | Lys | Asn | Gly | Glu | Val | Ala | |
| | | 80 | | | | | 85 | | | | |

| GCA | ACC | AAA | GTG | GGT | GCA | CTG | TCT | AAA | GGT | CAG | 2538 |
|---|---|---|---|---|---|---|---|---|---|---|---|
| Ala | Thr | Lys | Val | Gly | Ala | Leu | Ser | Lys | Gly | Gln | |
| | 90 | | | | | 95 | | | | | |

| TTG | AAA | GAG | TTC | CTC | GAC | GCT | AAC | CTG | GCC | GGT | 2571 |
|---|---|---|---|---|---|---|---|---|---|---|---|
| Leu | Lys | Glu | Phe | Leu | Asp | Ala | Asn | Leu | Ala | Gly | |
| 100 | | | | | 105 | | | | | 110 | |

| TCT | GGT | TCT | GGT | GAT | GAC | GAT | GAC | AAA | GGT | CCA | 2604 |
|---|---|---|---|---|---|---|---|---|---|---|---|
| Ser | Gly | Ser | Gly | Asp | Asp | Asp | Asp | Lys | Gly | Pro | |
| | | | | 115 | | | | | 120 | | |

| CCA | CCA | GGT | CCA | CCT | CGA | GTT | TCC | CCA | GAC | CCT | 2637 |
|---|---|---|---|---|---|---|---|---|---|---|---|
| Pro | Pro | Gly | Pro | Pro | Arg | Val | Ser | Pro | Asp | Pro | |
| | | | 125 | | | | | 130 | | | |

| CGG | GCC | GAG | CTG | GAC | AGC | ACC | GTG | CTC | CTG | ACC | 2670 |
|---|---|---|---|---|---|---|---|---|---|---|---|
| Arg | Ala | Glu | Leu | Asp | Ser | Thr | Val | Leu | Leu | Thr | |
| | | 135 | | | | | 140 | | | | |

FIGURE 2C

| | | | | | | | | | | |
|---|---|---|---|---|---|---|---|---|---|---|
| CGC | TCT | CTC | CTG | GCG | GAC | ACG | CGG | CAG | CTG | GCT | 2703 |
| Arg | Ser | Leu | Leu | Ala | Asp | Thr | Arg | Gln | Leu | Ala | |
| | 145 | | | | 150 | | | | | | |
| GCA | CAG | CTG | AGG | GAC | AAA | TTC | CCA | GCT | GAC | GGG | 2736 |
| Ala | Gln | Leu | Arg | Asp | Lys | Phe | Pro | Ala | Asp | Gly | |
| 155 | | | | | 160 | | | | | 165 | |
| GAC | CAC | AAC | CTG | GAT | TCC | CTG | CCC | ACC | CTG | GCC | 2769 |
| Asp | His | Asn | Leu | Asp | Ser | Leu | Pro | Thr | Leu | Ala | |
| | | | | 170 | | | | | 175 | | |
| ATG | AGT | GCG | GGG | GCA | CTG | GGA | GCT | CTA | CAG | CTC | 2802 |
| Met | Ser | Ala | Gly | Ala | Leu | Gly | Ala | Leu | Gln | Leu | |
| | | | 180 | | | | 185 | | | | |
| CCA | GGT | GTG | CTG | ACA | AGG | CTG | CGA | GCG | GAC | CTA | 2835 |
| Pro | Gly | Val | Leu | Thr | Arg | Leu | Arg | Ala | Asp | Leu | |
| | | | 190 | | | | | 195 | | | |
| CTG | TCC | TAC | CTG | CGG | CAC | GTG | CAG | TGG | CTG | CGC | 2868 |
| Leu | Ser | Tyr | Leu | Arg | His | Val | Gln | Trp | Leu | Arg | |
| | | 200 | | | | | 205 | | | | |
| CGG | GCA | GGT | GGC | TCT | TCC | CTG | AAG | ACC | CTG | GAG | 2901 |
| Arg | Ala | Gly | Gly | Ser | Ser | Leu | Lys | Thr | Leu | Glu | |
| 210 | | | | | 215 | | | | | 220 | |
| CCC | GAG | CTG | GGC | ACC | CTG | CAG | GCC | CGA | CTG | GAC | 2934 |
| Pro | Glu | Leu | Gly | Thr | Leu | Gln | Ala | Arg | Leu | Asp | |
| | | | | 225 | | | | | 230 | | |
| CGG | CTG | CTG | CGC | CGG | CTG | CAG | CTC | CTG | ATG | TCC | 2967 |
| Arg | Leu | Leu | Arg | Arg | Leu | Gln | Leu | Leu | Met | Ser | |
| | | | | 235 | | | | | 240 | | |
| CGC | CTG | GCC | CTG | CCC | CAG | CCA | CCC | CCG | GAC | CCG | 3000 |
| Arg | Leu | Ala | Leu | Pro | Gln | Pro | Pro | Pro | Asp | Pro | |
| | | | 245 | | | | | 250 | | | |
| CCG | GCG | CCC | CCG | CTG | GCG | CCC | CCC | TCC | TCA | GCC | 3033 |
| Pro | Ala | Pro | Pro | Leu | Ala | Pro | Pro | Ser | Ser | Ala | |
| | 255 | | | | | 260 | | | | | |
| TGG | GGG | GGC | ATC | AGG | GCC | GCC | CAC | GCC | ATC | CTG | 3066 |
| Trp | Gly | Gly | Ile | Arg | Ala | Ala | His | Ala | Ile | Leu | |
| 265 | | | | | 270 | | | | | 275 | |
| GGG | GGG | CTG | CAC | CTG | ACA | CTT | GAC | TGG | GCC | GTG | 3099 |
| Gly | Gly | Leu | His | Leu | Thr | Leu | Asp | Trp | Ala | Val | |
| | | | | 280 | | | | | 285 | | |
| AGG | GGA | CTG | CTG | CTG | CTG | AAG | ACT | CGG | CTG | TGA | 3132 |
| Arg | Gly | Leu | Leu | Leu | Leu | Lys | Thr | Arg | Leu | | |
| | | | | 290 | | | | | 295 | | |

FIGURE 2D

| | | | | |
|---|---|---|---|---|
| AAGCTTATCG | ATACCGTCGA | CCTGCAGTAA | TCGTACAGGG | 3172 |
| TAGTACAAAT | AAAAAAGGCA | CGTCAGATGA | CGTGCCTTTT | 3212 |
| TTCTTGTGAG | CAGTAAGCTT | GGCACTGGCC | GTCGTTTTAC | 3252 |
| AACGTCGTGA | CTGGGAAAAC | CCTGGCGTTA | CCCAACTTAA | 3292 |
| TCGCCTTGCA | GCACATCCCC | CTTTCGCCAG | CTGGCGTAAT | 3332 |
| AGCGAAGAGG | CCCGCACCGA | TCGCCTTCC | CAACAGTTGC | 3372 |
| GCAGCCTGAA | TGGCGAATGG | CGCCTGATGC | GGTATTTTCT | 3412 |
| CCTTACGCAT | CTGTGCGGTA | TTTCACACCG | CATATATGGT | 3452 |
| GCACTCTCAG | TACAATCTGC | TCTGATGCCG | CATAGTTAAG | 3492 |
| CCAGCCCCGA | CACCCGCCAA | CACCCGCTGA | CGCGCCCTGA | 3532 |
| CGGGCTTGTC | TGCTCCCGGC | ATCCGCTTAC | AGACAAGCTG | 3572 |
| TGACCGTCTC | CGGGAGCTGC | ATGTGTCAGA | GGTTTTCACC | 3612 |
| GTCATCACCG | AAACGCGCGA | | | 3632 |

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 977 base pairs
( B ) TYPE: nucleic acid
( C ) STRANDEDNESS: double
( D ) TOPOLOGY: unknown ( i i ) MOLECULE TYPE: DNA (genomic)

( i x ) FEATURE:
( A ) NAME/KEY: CDS
( B ) LOCATION: 70..666

( x i ) SEQUENCE DESCRIPTION: SEQ ID NO:1:

```
AGCTGGGAAG GGTTAAAGGC CCCCGGCTCC CTGCCCCCTG CCCTGGGGAA CCCCTGGCCC      60
```

| | |
|---|---|
| TGCGGGGAC ATG AAC TGT GTT TGC CGC CTG GTC CTG GTC GTG CTG AGC<br>            Met Asn Cys Val Cys Arg Leu Val Leu Val Val Leu Ser<br>             1                     5                           10 | 108 |
| CTG TGG CCA GAT ACA GCT GTC GCC CCT GGG CCA CCA CCT GGC CCC CCT<br>Leu Trp Pro Asp Thr Ala Val Ala Pro Gly Pro Pro Pro Gly Pro Pro<br>    15                        20                        25 | 156 |
| CGA GTT TCC CCA GAC CCT CGG GCC GAG CTG GAC AGC ACC GTG CTC CTG<br>Arg Val Ser Pro Asp Pro Arg Ala Glu Leu Asp Ser Thr Val Leu Leu<br>30                        35                        40                       45 | 204 |
| ACC CGC TCT CTC CTG GCG GAC ACG CGG CAG CTG GCT GCA CAG CTG AGG<br>Thr Arg Ser Leu Leu Ala Asp Thr Arg Gln Leu Ala Ala Gln Leu Arg<br>                  50                        55                       60 | 252 |
| GAC AAA TTC CCA GCT GAC GGG GAC CAC AAC CTG GAT TCC CTG CCC ACC<br>Asp Lys Phe Pro Ala Asp Gly Asp His Asn Leu Asp Ser Leu Pro Thr<br>             65                             70                        75 | 300 |
| CTG GCC ATG AGT GCG GGG GCA CTG GGA GCT CTA CAG CTC CCA GGT GTG<br>Leu Ala Met Ser Ala Gly Ala Leu Gly Ala Leu Gln Leu Pro Gly Val<br>        80                        85                        90 | 348 |
| CTG ACA AGG CTG CGA GCG GAC CTA CTG TCC TAC CTG CGG CAC GTG CAG<br>Leu Thr Arg Leu Arg Ala Asp Leu Leu Ser Tyr Leu Arg His Val Gln<br>    95                      100                      105 | 396 |
| TGG CTG CGC CGG GCA GGT GGC TCT TCC CTG AAG ACC CTG GAG CCC GAG<br>Trp Leu Arg Arg Ala Gly Gly Ser Ser Leu Lys Thr Leu Glu Pro Glu<br>110                       115                      120                      125 | 444 |
| CTG GGC ACC CTG CAG GCC CGA CTG GAC CGG CTG CTG CGC CGG CTG CAG<br>Leu Gly Thr Leu Gln Ala Arg Leu Asp Arg Leu Leu Arg Arg Leu Gln<br>            130                           135                      140 | 492 |
| CTC CTG ATG TCC CGC CTG GCC CTG CCC CAG CCA CCC CCG GAC CCG CCG<br>Leu Leu Met Ser Arg Leu Ala Leu Pro Gln Pro Pro Pro Asp Pro Pro<br>              145                        150                      155 | 540 |
| GCG CCC CCG CTG GCG CCC CCC TCC TCA GCC TGG GGG GGC ATC AGG GCC<br>Ala Pro Pro Leu Ala Pro Pro Ser Ser Ala Trp Gly Gly Ile Arg Ala<br>            160                         165                      170 | 588 |
| GCC CAC GCC ATC CTG GGG GGG CTG CAC CTG ACA CTT GAC TGG GCC GTG<br>Ala His Ala Ile Leu Gly Gly Leu His Leu Thr Leu Asp Trp Ala Val<br>175                       180                      185 | 636 |
| AGG GGA CTG CTG CTG CTG AAG ACT CGG CTG TGACCCGAGG CCCAGAGCCA<br>Arg Gly Leu Leu Leu Leu Lys Thr Arg Leu<br>190                       195 | 686 |
| CCACCGTCCT TCCAAAGCCA CATCTTATTT ATTTATTTAT TTCGGTACTG GGGGCGAAAC | 746 |
| AGCCAGGTGA TCCCCCTGCC TTTAGCTCCC CCTAGTTAGA GACAGTCCTT CCGTGAGGCT | 806 |
| GGGGGGCATC TGTGCCTTAT TTATACTTAT TTATTTCAGG AGCGGGGGTG GGCTCCTGGG | 866 |
| TCCCCGAGGA GGAGGGAGCT GGGGTCCCGG ATTCTTGTGT CCACAGACTT CTGCCCTGGC | 926 |
| TCCTCCCCCT CGAGGCCTGG GCAGGAATAC ATACTATTTA TTTAAGAGCT C | 977 |

( 2 ) INFORMATION FOR SEQ ID NO:2:

( i ) SEQUENCE CHARACTERISTICS:
        ( A ) LENGTH: 199 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

Met Asn Cys Val Cys Arg Leu Val Leu Val Val Leu Ser Leu Trp Pro
1                    5                    10                    15

Asp Thr Ala Val Ala Pro Gly Pro Pro Pro Gly Pro Pro Arg Val Ser
                20                    25                    30

Pro Asp Pro Arg Ala Glu Leu Asp Ser Thr Val Leu Leu Thr Arg Ser
                35                    40                    45

```
Leu Leu Ala Asp Thr Arg Gln Leu Ala Ala Gln Leu Arg Asp Lys Phe
     50                  55                  60

Pro Ala Asp Gly Asp His Asn Leu Asp Ser Leu Pro Thr Leu Ala Met
 65                  70                  75                   80

Ser Ala Gly Ala Leu Gly Ala Leu Gln Leu Pro Gly Val Leu Thr Arg
                 85                  90                   95

Leu Arg Ala Asp Leu Leu Ser Tyr Leu Arg His Val Gln Trp Leu Arg
             100                 105                 110

Arg Ala Gly Gly Ser Ser Leu Lys Thr Leu Glu Pro Glu Leu Gly Thr
             115                 120                 125

Leu Gln Ala Arg Leu Asp Arg Leu Leu Arg Arg Leu Gln Leu Leu Met
    130                 135                 140

Ser Arg Leu Ala Leu Pro Gln Pro Pro Pro Asp Pro Pro Ala Pro Pro
145                 150                 155                 160

Leu Ala Pro Pro Ser Ser Ala Trp Gly Gly Ile Arg Ala Ala His Ala
                 165                 170                 175

Ile Leu Gly Gly Leu His Leu Thr Leu Asp Trp Ala Val Arg Gly Leu
             180                 185                 190

Leu Leu Leu Lys Thr Arg Leu
             195
```

( 2 ) INFORMATION FOR SEQ ID NO:3:

( i ) SEQUENCE CHARACTERISTICS:
        ( A ) LENGTH: 3632 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 2242..3132

( i x ) FEATURE:
        ( A ) NAME/KEY: misc_feature
        ( B ) LOCATION: 2242..2568
        ( D ) OTHER INFORMATION: /product="E. coli thioredoxin
            protein"
            / note="Lim et al, J. Bacteriol., 163:311-316
            ( 1 9 8 5 )"

( i x ) FEATURE:
        ( A ) NAME/KEY: RBS
        ( B ) LOCATION: 2222..2241
        ( D ) OTHER INFORMATION: /standard_name="ribosome binding
            sequence"
            / note="Dunn and Studier, J. Mol. Biol,
            166:477-535 (1983)"

( i x ) FEATURE:
        ( A ) NAME/KEY: misc_feature
        ( B ) LOCATION: 2061..2221
        ( D ) OTHER INFORMATION: /function="leftward promoter of
            bacteriophage lambda"
            / note="Sanger et al, J. Mol. Biol, 162:729-773
            ( 1 9 8 2 )"

( i x ) FEATURE:
        ( A ) NAME/KEY: misc_feature
        ( B ) LOCATION: 1..2060
        ( D ) OTHER INFORMATION: /function="derived from plasmid
            pUC-18"
            / note="Norrander et al, Gene, 26:101-106 (1983)"

( i x ) FEATURE:
        ( A ) NAME/KEY: misc_feature
        ( B ) LOCATION: 2569..2583
        ( D ) OTHER INFORMATION: /function="short, hydrophilic
            flexible spacer peptide"

( i x ) FEATURE:
    ( A ) NAME/KEY: misc_feature
    ( B ) LOCATION: 2584..2598
    ( D ) OTHER INFORMATION: /function="enterokinase cleavage recognition site"
    / note="Maroux et al, J. Biol. Chem., 246:5031- 5039 (1971)"

( i x ) FEATURE:
    ( A ) NAME/KEY: misc_feature
    ( B ) LOCATION: 2599..3132
    ( D ) OTHER INFORMATION: /product="modified form of mature human IL11"
    / note="Paul et al, Proc. Natl. Acad. Sci. USA, 87:7512-7516 (1990)"

( i x ) FEATURE:
    ( A ) NAME/KEY: misc_feature
    ( B ) LOCATION: 3133..3159
    ( D ) OTHER INFORMATION: /function="linker sequence containing restriction endonuclease sites"

( i x ) FEATURE:
    ( A ) NAME/KEY: misc_feature
    ( B ) LOCATION: 3160..3232
    ( D ) OTHER INFORMATION: /function="transcription termination sequence based on E. coli aspA"
    / note="Takagi et al, Nucl. Acids Res., 13:2063-2074 (1985)"

( i x ) FEATURE:
    ( A ) NAME/KEY: misc_feature
    ( B ) LOCATION: 3233..3632
    ( D ) OTHER INFORMATION: /function="DNA sequences derived from pUC- 18"

( x i ) SEQUENCE DESCRIPTION: SEQ ID NO:3:

```
GACGAAAGGG  CCTCGTGATA  CGCCTATTTT  TATAGGTTAA  TGTCATGATA  ATAATGGTTT      60
CTTAGACGTC  AGGTGGCACT  TTTCGGGGAA  ATGTGCGCGG  AACCCCTATT  TGTTTATTTT     120
TCTAAATACA  TTCAAATATG  TATCCGCTCA  TGAGACAATA  ACCCTGATAA  ATGCTTCAAT     180
AATATTGAAA  AAGGAAGAGT  ATGAGTATTC  AACATTTCCG  TGTCGCCCTT  ATTCCCTTTT     240
TTGCGGCATT  TTGCCTTCCT  GTTTTTGCTC  ACCCAGAAAC  GCTGGTGAAA  GTAAAAGATG     300
CTGAAGATCA  GTTGGGTGCA  CGAGTGGGTT  ACATCGAACT  GGATCTCAAC  AGCGGTAAGA     360
TCCTTGAGAG  TTTTCGCCCC  GAAGAACGTT  TTCCAATGAT  GAGCACTTTT  AAAGTTCTGC     420
TATGTGGCGC  GGTATTATCC  CGTATTGACG  CCGGGCAAGA  GCAACTCGGT  CGCCGCATAC     480
ACTATTCTCA  GAATGACTTG  GTTGAGTACT  CACCAGTCAC  AGAAAAGCAT  CTTACGGATG     540
GCATGACAGT  AAGAGAATTA  TGCAGTGCTG  CCATAACCAT  GAGTGATAAC  ACTGCGGCCA     600
ACTTACTTCT  GACAACGATC  GGAGGACCGA  AGGAGCTAAC  CGCTTTTTTG  CACAACATGG     660
GGGATCATGT  AACTCGCCTT  GATCGTTGGG  AACCGGAGCT  GAATGAAGCC  ATACCAAACG     720
ACGAGCGTGA  CACCACGATG  CCTGTAGCAA  TGGCAACAAC  GTTGCGCAAA  CTATTAACTG     780
GCGAACTACT  TACTCTAGCT  TCCCGGCAAC  AATTAATAGA  CTGGATGGAG  GCGGATAAAG     840
TTGCAGGACC  ACTTCTGCGC  TCGGCCCTTC  CGGCTGGCTG  GTTTATTGCT  GATAAATCTG     900
GAGCCGGTGA  GCGTGGGTCT  CGCGGTATCA  TTGCAGCACT  GGGGCCAGAT  GGTAAGCCCT     960
CCCGTATCGT  AGTTATCTAC  ACGACGGGGA  GTCAGGCAAC  TATGGATGAA  CGAAATAGAC    1020
AGATCGCTGA  GATAGGTGCC  TCACTGATTA  AGCATTGGTA  ACTGTCAGAC  CAAGTTTACT    1080
CATATATACT  TTAGATTGAT  TTAAAACTTC  ATTTTTAATT  TAAAAGGATC  TAGGTGAAGA    1140
TCCTTTTTGA  TAATCTCATG  ACCAAAATCC  CTTAACGTGA  GTTTTCGTTC  CACTGAGCGT    1200
CAGACCCCGT  AGAAAAGATC  AAAGGATCTT  CTTGAGATCC  TTTTTTTCTG  CGCGTAATCT    1260
GCTGCTTGCA  AACAAAAAAA  CCACCGCTAC  CAGCGGTGGT  TTGTTTGCCG  GATCAAGAGC    1320
```

```
TACCAACTCT TTTTCCGAAG GTAACTGGCT TCAGCAGAGC GCAGATACCA AATACTGTCC    1380

TTCTAGTGTA GCCGTAGTTA GGCCACCACT TCAAGAACTC TGTAGCACCG CCTACATACC    1440

TCGCTCTGCT AATCCTGTTA CCAGTGGCTG CTGCCAGTGG CGATAAGTCG TGTCTTACCG    1500

GGTTGGACTC AAGACGATAG TTACCGGATA AGGCGCAGCG GTCGGGCTGA ACGGGGGGTT    1560

CGTGCACACA GCCCAGCTTG GAGCGAACGA CCTACACCGA ACTGAGATAC CTACAGCGTG    1620

AGCATTGAGA AAGCGCCACG CTTCCCGAAG GGAGAAAGGC GGACAGGTAT CCGGTAAGCG    1680

GCAGGGTCGG AACAGGAGAG CGCACGAGGG AGCTTCCAGG GGGAAACGCC TGGTATCTTT    1740

ATAGTCCTGT CGGGTTTCGC CACCTCTGAC TTGAGCGTCG ATTTTGTGA TGCTCGTCAG     1800

GGGGGCGGAG CCTATGGAAA AACGCCAGCA ACGCGGCCTT TTTACGGTTC CTGGCCTTTT    1860

GCTGGCCTTT TGCTCACATG TTCTTTCCTG CGTTATCCCC TGATTCTGTG GATAACCGTA    1920

TTACCGCCTT TGAGTGAGCT GATACCGCTC GCCGCAGCCG AACGACCGAG CGCAGCGAGT    1980

CAGTGAGCGA GGAAGCGGAA GAGCGCCCAA TACGCAAACC GCCTCTCCCC GCGCGTTGGC    2040

CGATTCATTA ATGCAGAATT GATCTCTCAC CTACCAAACA ATGCCCCCT GCAAAAATA     2100

AATTCATATA AAAACATAC AGATAACCAT CTGCGGTGAT AAATTATCTC TGGCGGTGTT    2160

GACATAAATA CCACTGGCGG TGATACTGAG CACATCAGCA GGACGCACTG ACCACCATGA    2220

ATTCAAGAAG GAGATATACA T ATG AGC GAT AAA ATT ATT CAC CTG ACT GAC    2271
                        Met Ser Asp Lys Ile Ile His Leu Thr Asp
                        1               5                   10

GAC AGT TTT GAC ACG GAT GTA CTC AAA GCG GAC GGG GCG ATC CTC GTC    2319
Asp Ser Phe Asp Thr Asp Val Leu Lys Ala Asp Gly Ala Ile Leu Val
            15                  20                  25

GAT TTC TGG GCA GAG TGG TGC GGT CCG TGC AAA ATG ATC GCC CCG ATT    2367
Asp Phe Trp Ala Glu Trp Cys Gly Pro Cys Lys Met Ile Ala Pro Ile
        30                  35                  40

CTG GAT GAA ATC GCT GAC GAA TAT CAG GGC AAA CTG ACC GTT GCA AAA    2415
Leu Asp Glu Ile Ala Asp Glu Tyr Gln Gly Lys Leu Thr Val Ala Lys
    45                  50                  55

CTG AAC ATC GAT CAA AAC CCT GGC ACT GCG CCG AAA TAT GGC ATC CGT    2463
Leu Asn Ile Asp Gln Asn Pro Gly Thr Ala Pro Lys Tyr Gly Ile Arg
60                  65                  70

GGT ATC CCG ACT CTG CTG CTG TTC AAA AAC GGT GAA GTG GCG GCA ACC    2511
Gly Ile Pro Thr Leu Leu Leu Phe Lys Asn Gly Glu Val Ala Ala Thr
75                  80                  85                  90

AAA GTG GGT GCA CTG TCT AAA GGT CAG TTG AAA GAG TTC CTC GAC GCT    2559
Lys Val Gly Ala Leu Ser Lys Gly Gln Leu Lys Glu Phe Leu Asp Ala
                95                  100                 105

AAC CTG GCC GGT TCT GGT TCT GGT GAT GAC GAT GAC AAA GGT CCA CCA    2607
Asn Leu Ala Gly Ser Gly Ser Gly Asp Asp Asp Asp Lys Gly Pro Pro
            110                 115                 120

CCA GGT CCA CCT CGA GTT TCC CCA GAC CCT CGG GCC GAG CTG GAC AGC    2655
Pro Gly Pro Pro Arg Val Ser Pro Asp Pro Arg Ala Glu Leu Asp Ser
        125                 130                 135

ACC GTG CTC CTG ACC CGC TCT CTC CTG GCG GAC ACG CGG CAG CTG GCT    2703
Thr Val Leu Leu Thr Arg Ser Leu Leu Ala Asp Thr Arg Gln Leu Ala
    140                 145                 150

GCA CAG CTG AGG GAC AAA TTC CCA GCT GAC GGG GAC CAC AAC CTG GAT    2751
Ala Gln Leu Arg Asp Lys Phe Pro Ala Asp Gly Asp His Asn Leu Asp
155                 160                 165                 170

TCC CTG CCC ACC CTG GCC ATG AGT GCG GGG GCA CTG GGA GCT CTA CAG    2799
Ser Leu Pro Thr Leu Ala Met Ser Ala Gly Ala Leu Gly Ala Leu Gln
            175                 180                 185

CTC CCA GGT GTG CTG ACA AGG CTG CGA GCG GAC CTA CTG TCC TAC CTG    2847
Leu Pro Gly Val Leu Thr Arg Leu Arg Ala Asp Leu Leu Ser Tyr Leu
        190                 195                 200
```

| | | | | | | | | | | | | | | | | |
|---|---|---|---|---|---|---|---|---|---|---|---|---|---|---|---|---|
| CGG | CAC | GTG | CAG | TGG | CTG | CGC | CGG | GCA | GGT | GGC | TCT | TCC | CTG | AAG | ACC | 2895 |
| Arg | His | Val | Gln | Trp | Leu | Arg | Arg | Ala | Gly | Gly | Ser | Ser | Leu | Lys | Thr | |
| | | 205 | | | | | 210 | | | | 215 | | | | | |
| CTG | GAG | CCC | GAG | CTG | GGC | ACC | CTG | CAG | GCC | CGA | CTG | GAC | CGG | CTG | CTG | 2943 |
| Leu | Glu | Pro | Glu | Leu | Gly | Thr | Leu | Gln | Ala | Arg | Leu | Asp | Arg | Leu | Leu | |
| | 220 | | | | | 225 | | | | | 230 | | | | | |
| CGC | CGG | CTG | CAG | CTC | CTG | ATG | TCC | CGC | CTG | GCC | CTG | CCC | CAG | CCA | CCC | 2991 |
| Arg | Arg | Leu | Gln | Leu | Leu | Met | Ser | Arg | Leu | Ala | Leu | Pro | Gln | Pro | Pro | |
| 235 | | | | | 240 | | | | | 245 | | | | | 250 | |
| CCG | GAC | CCG | CCG | GCG | CCC | CCG | CTG | GCG | CCC | CCC | TCC | TCA | GCC | TGG | GGG | 3039 |
| Pro | Asp | Pro | Pro | Ala | Pro | Pro | Leu | Ala | Pro | Pro | Ser | Ser | Ala | Trp | Gly | |
| | | | | 255 | | | | | 260 | | | | | 265 | | |
| GGC | ATC | AGG | GCC | GCC | CAC | GCC | ATC | CTG | GGG | GGG | CTG | CAC | CTG | ACA | CTT | 3087 |
| Gly | Ile | Arg | Ala | Ala | His | Ala | Ile | Leu | Gly | Gly | Leu | His | Leu | Thr | Leu | |
| | | | 270 | | | | | 275 | | | | | 280 | | | |
| GAC | TGG | GCC | GTG | AGG | GGA | CTG | CTG | CTG | CTG | AAG | ACT | CGG | CTG | TGAAAGCTTA | | 3139 |
| Asp | Trp | Ala | Val | Arg | Gly | Leu | Leu | Leu | Leu | Lys | Thr | Arg | Leu | | | |
| | | 285 | | | | | 290 | | | | | 295 | | | | |

| | | | | | |
|---|---|---|---|---|---|
| TCGATACCGT | CGACCTGCAG | TAATCGTACA | GGGTAGTACA | AATAAAAAAG | GCACGTCAGA | 3199 |
| TGACGTGCCT | TTTTTCTTGT | GAGCAGTAAG | CTTGGCACTG | GCCGTCGTTT | ACAACGTCG | 3259 |
| TGACTGGGAA | AACCCTGGCG | TTACCCAACT | TAATCGCCTT | GCAGCACATC | CCCCTTTCGC | 3319 |
| CAGCTGGCGT | AATAGCGAAG | AGGCCCGCAC | CGATCGCCCT | TCCCAACAGT | TGCGCAGCCT | 3379 |
| GAATGGCGAA | TGGCGCCTGA | TGCGGTATTT | TCTCCTTACG | CATCTGTGCG | GTATTTCACA | 3439 |
| CCGCATATAT | GGTGCACTCT | CAGTACAATC | TGCTCTGATG | CCGCATAGTT | AAGCCAGCCC | 3499 |
| CGACACCCGC | CAACACCCGC | TGACGCGCCC | TGACGGGCTT | GTCTGCTCCC | GGCATCCGCT | 3559 |
| TACAGACAAG | CTGTGACCGT | CTCCGGGAGC | TGCATGTGTC | AGAGGTTTTC | ACCGTCATCA | 3619 |
| CCGAAACGCG | CGA | | | | | 3632 |

( 2 ) INFORMATION FOR SEQ ID NO:4:

( i ) SEQUENCE CHARACTERISTICS:
        ( A ) LENGTH: 296 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
| Met | Ser | Asp | Lys | Ile | Ile | His | Leu | Thr | Asp | Asp | Ser | Phe | Asp | Thr | Asp |
| 1 | | | | 5 | | | | | 10 | | | | | 15 | |
| Val | Leu | Lys | Ala | Asp | Gly | Ala | Ile | Leu | Val | Asp | Phe | Trp | Ala | Glu | Trp |
| | | | 20 | | | | | 25 | | | | | 30 | | |
| Cys | Gly | Pro | Cys | Lys | Met | Ile | Ala | Pro | Ile | Leu | Asp | Glu | Ile | Ala | Asp |
| | | | 35 | | | | 40 | | | | | 45 | | | |
| Glu | Tyr | Gln | Gly | Lys | Leu | Thr | Val | Ala | Lys | Leu | Asn | Ile | Asp | Gln | Asn |
| | 50 | | | | | 55 | | | | | 60 | | | | |
| Pro | Gly | Thr | Ala | Pro | Lys | Tyr | Gly | Ile | Arg | Gly | Ile | Pro | Thr | Leu | Leu |
| 65 | | | | | 70 | | | | | 75 | | | | | 80 |
| Leu | Phe | Lys | Asn | Gly | Glu | Val | Ala | Ala | Thr | Lys | Val | Gly | Ala | Leu | Ser |
| | | | | 85 | | | | | 90 | | | | | 95 | |
| Lys | Gly | Gln | Leu | Lys | Glu | Phe | Leu | Asp | Ala | Asn | Leu | Ala | Gly | Ser | Gly |
| | | | 100 | | | | | 105 | | | | | 110 | | |
| Ser | Gly | Asp | Asp | Asp | Asp | Lys | Gly | Pro | Pro | Pro | Gly | Pro | Pro | Arg | Val |
| | | 115 | | | | | 120 | | | | | 125 | | | |
| Ser | Pro | Asp | Pro | Arg | Ala | Glu | Leu | Asp | Ser | Thr | Val | Leu | Leu | Thr | Arg |
| | 130 | | | | | 135 | | | | | 140 | | | | |

```
Ser Leu Leu Ala Asp Thr Arg Gln Leu Ala Ala Gln Leu Arg Asp Lys
145             150                 155                 160

Phe Pro Ala Asp Gly Asp His Asn Leu Asp Ser Leu Pro Thr Leu Ala
            165                     170                 175

Met Ser Ala Gly Ala Leu Gly Ala Leu Gln Leu Pro Gly Val Leu Thr
            180                 185                 190

Arg Leu Arg Ala Asp Leu Leu Ser Tyr Leu Arg His Val Gln Trp Leu
        195                 200                 205

Arg Arg Ala Gly Gly Ser Ser Leu Lys Thr Leu Glu Pro Glu Leu Gly
    210                 215                 220

Thr Leu Gln Ala Arg Leu Asp Arg Leu Leu Arg Arg Leu Gln Leu Leu
225                 230                 235                 240

Met Ser Arg Leu Ala Leu Pro Gln Pro Pro Pro Asp Pro Pro Ala Pro
                245                 250                 255

Pro Leu Ala Pro Pro Ser Ser Ala Trp Gly Gly Ile Arg Ala Ala His
            260                 265                 270

Ala Ile Leu Gly Gly Leu His Leu Thr Leu Asp Trp Ala Val Arg Gly
        275                 280                 285

Leu Leu Leu Leu Lys Thr Arg Leu
290                 295
```

METHOD OF ENHANCING THE GROWTH OF GUT EPITHELIAL CELLS BY ADMINISTRATION OF A CYTOKINE SUCH AS INTERLEUKIN II

This work was supported by grants by the National Institutes of Health Grant Nos. 1 PO1 HL45168-01A1 and 1RO1 HL46528-01. The government has certain rights in this invention.

CROSS-REFERENCE TO RELATED APPLICATION

This is a continuation-in-part of U.S. patent application Ser. No. 941,372, filed Sep. 2, 1992, now pending.

FIELD OF THE INVENTION

This invention provides a method of treating patients having disorders characterized by cell damage or destruction, and more specifically, a method of using a cytokine to regenerate populations of certain cells, particularly gut cells.

BACKGROUND OF THE INVENTION

Certain mammalian cells in their normal state are characterized by rapid division and proliferation in the body, e.g., small intestinal epithelial cells, sperm cells, hair and skin cells, and hepatocyte or liver cells. Damage to, or depletion of, these cells can result due to certain diseases, infections, exposure to therapeutic agents and treatments, exposure to other chemical or biological agents, and injury or trauma.

For example, the use of chemotherapy and radiation therapy for the treatment of cancer and for the preparation of patients for bone marrow transplantation is toxic to the small intestinal (gut) epithelial cells. In fact, the small intestine is one of the organs most damaged by this therapy. Similarly damaged by such therapy are skin cells, hair cells and sperm cells. This cell damage, particularly to the gut cells, is the cause of significant mortality and morbidity in cancer patients undergoing therapy. Previously, such toxicity has been avoided by limiting the amount of chemotherapy or radiation administered to the patient. For example, gut cell toxicity has been diminished with radiation therapy by both decreasing the amount of radiation and giving the total dose subdivided into fractions (called 'fractionation' therapy). However, the reduced amount of therapy also has an adverse effect on the spread and growth of the cancer against which it is directed.

Certain autoimmune diseases of the gut, such as Crohn's disease and ulcerative colitis, also have been known to damage the small intestinal cells lining the gut, causing major morbidity and mortality in patients so afflicted. Treatment of autoimmune diseases of the gut include chemotherapy and immune suppression, both of which have serious side effects, among them additional damage to the rapidly dividing gut cells.

Skin and hair cell populations may also be damaged by autoimmune diseases, burns, and alopecia. Sperm cell populations are damaged by oligospermia. Hepatocytes are also damaged by radiation, chemotherapy, and physical trauma.

Damage to gut cells, and to other cells which grow rapidly in a normal healthy mammal can also be the result of trauma or injury to the area, or shock. Exposure to certain industrial and household chemicals, among other agents, can also severely damage normal healthy populations of these cells.

There is a need in the art for methods for treating cell damage, particularly gut cell damage caused by disease or adverse effects of chemotherapeutic and radiation treatment, exposure to other damaging agents or trauma in mammals, particularly humans.

SUMMARY OF THE INVENTION

In one aspect, this invention provides a method for treating patients having damaged or depleted cell populations selected from the group consisting of small intestinal-epithelial cells, epithelial cells lining the large intestines and stomach, skin cells, hair cells, sperm cells and liver epithelial cells (hepatocytes). This method includes administering to the patient an effective amount of a selected hematopoietic growth factor or cytokine.

In another aspect, the invention provides a method of treating a patient undergoing chemotherapy or radiation therapy which involves administering a selected cytokine simultaneously with, or subsequently to, the initiation of chemotherapy or radiation treatment. The treatment with the cytokine is continued until a healthy cell population selected from the group consisting of small intestinal epithelial cells, epithelial cells lining the large intestines and stomach, skin cells, hair cells, sperm cells, and hepatocytes is restored.

In another aspect, the invention provides a method of restoring healthy cell populations selected from the group consisting of small intestinal epithelial cells, epithelial cells lining the large intestines and stomach, skin cells, hair cells, sperm cells, and liver epithelial cells in patients suffering from autoimmune conditions by administering to such patients effective amounts of a selected cytokine, particularly IL-11. It is anticipated that these cytokine treatments may be made in combination with currently known and used immunosuppressive therapies.

One or more cytokines alone or in combination useful in these methods may be selected from among interleukin-11, interleukin-6, leukemia inhibitory factor (LIF), Oncostatin M, and ciliary neurotrophic factor (CNTF). Additional cytokines which may be useful in this method include Interleukin-1, Interleukin-3, Interleukin-12 (also known as natural killer cell stimulatory factor) and GM-CSF.

Other aspects and advantages of the present invention are described further in the following detailed description of the preferred embodiments thereof.

BRIEF DESCRIPTION OF THE DRAWINGS

FIG. 1 provides the nucleic acid sequence [SEQ ID NO: 1] and predicted amino acid sequence (single letter code) [SEQ ID NO: 2] of human interleukin 11.

FIG. 2 illustrates the DNA sequence of the expression plasmid pALtrxA/EK/IL-11ΔPro-581 [SEQ ID NO: 3] and the amino acid sequence for the fusion protein therein [SEQ ID NO: 4], described in Example 2.

DETAILED DESCRIPTION OF THE INVENTION

Figure 3:
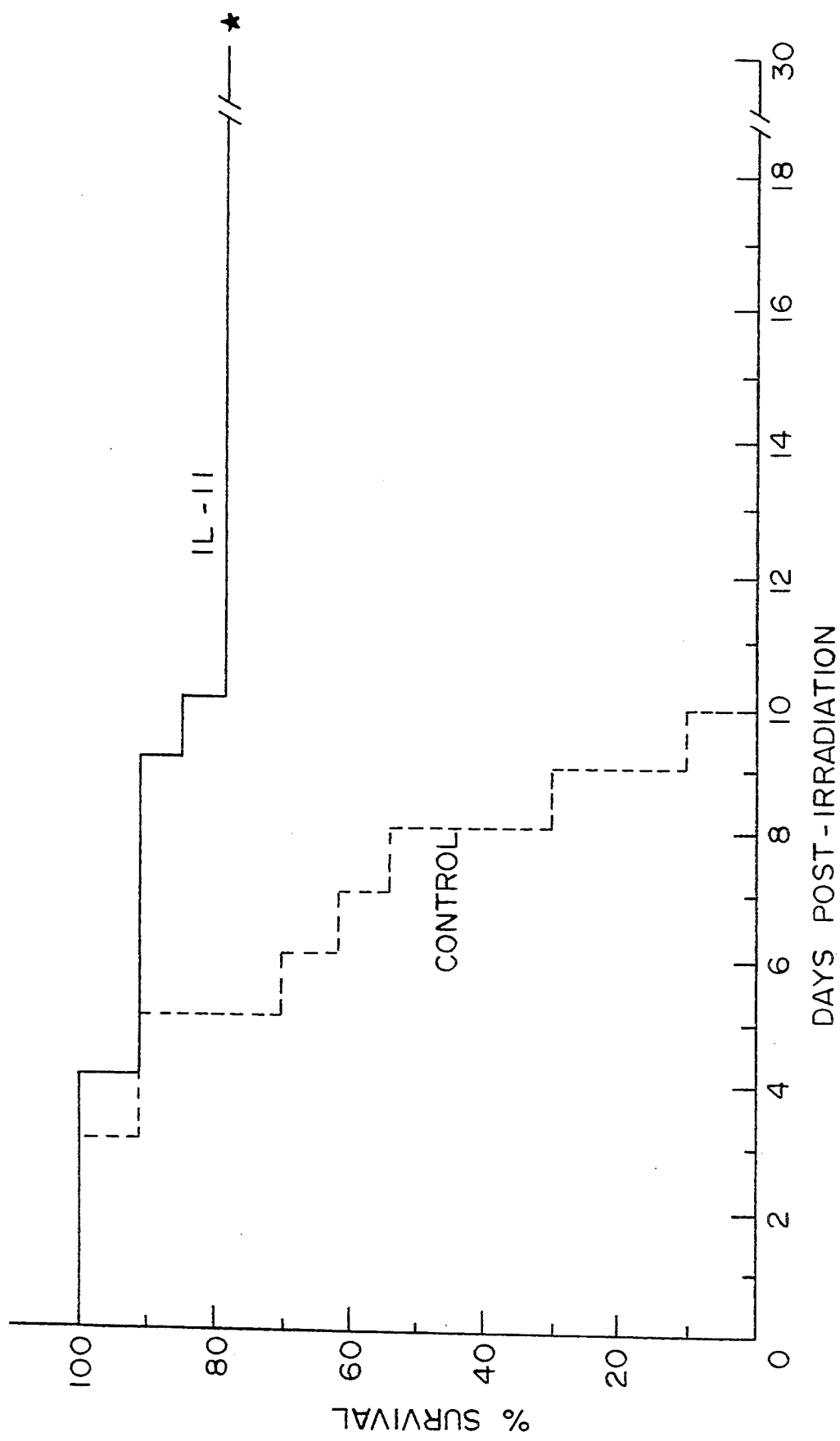
FIG. 3 is a graph illustrating the survival of control and IL-11 treated mice following combined chemotherapy and radiation treatment, as described in Example 5.
Figure 4:
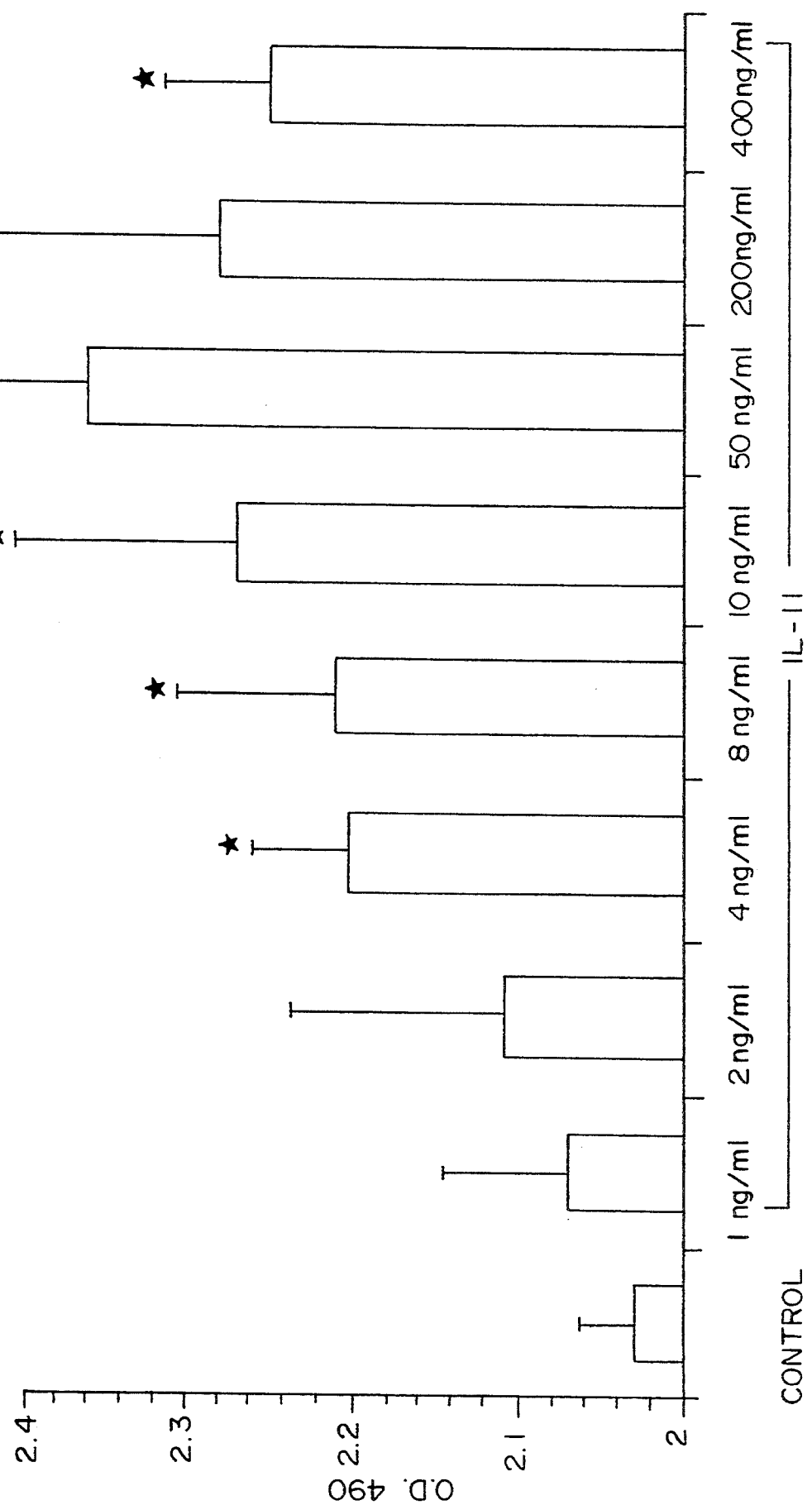
FIG. 4 is a bar graph illustrating the effect of IL-11 on proliferation of IEC-6 cells, as described in Example 9 below.

The invention provides a method of using a selected cytokine for the treatment of damaged or depleted cell populations, particularly those that are normally rapidly dividing populations. These include, but are not limited to, small intestinal epithelial cells, epithelial cells lining the large intestines and stomach, liver epithelial cells (hepatocytes), skin cells, hair cells, and sperm cells.

The methods of the present invention, which involve the administration of one or more selected cytokines, are useful in restoring populations of these cells regardless of the source or cause of the damage to, or depletion of, the cell population.

Cytokines are regulatory proteins that deliver signals between cells of the immune system, and have regulatory effects on cells of the hematopoietic and immune systems. One preferred cytokine for use in treating damaged cell populations is IL-11, a mammalian cytokine, which has been known to be useful in the treatment of selected diseases of the bone marrow and for directly or indirectly stimulating the production or function of B cells. IL-11 is described in detail in International Application, PCT/US90/06803, published May, 30, 1991.

The cloned human IL-11 sequence illustrated in FIG. 1 [SEQ ID NO:1 and 2], was deposited with the ATCC, 12301 Parklawn Drive, Rockville, Md. on Mar. 30, 1990 under ATCC No. 68284. Further, as described in the examples below, IL-11 may also be produced recombinantly as a fusion protein with another protein. FIG. 2 [SEQ ID NO:3 and 4] provides such a fusion sequence with *E. coli* thioredoxin. These sequences enable the production of IL-11 in a variety of host cells by resort to now conventional genetic engineering techniques.

IL-11 may also be obtained from certain cell lines. Human cell lines have been identified as sources of at least one species of IL-11 as in, for example, the human lung fibroblast cell line, MRC-5 (ATCC Accession Number CCL 171), and the human trophoblastic cell line, TPA30-1, (ATCC Accession Number CRL 1583). Other human sources for IL-11 may also be available. Additional information regarding the production of recombinant IL-11 and the isolation of IL-11 obtained from cell sources is provided in the above referenced International Application, PCT/US90/06803.

Not only is IL-11 useful in the methods of treating and restoring the cell populations above-described, but also, other cytokines are considered to be useful in the same methods. Certain cytokines which are characterized by having common signal transduction pathways with those of IL-11, (i.e., they transduce through gp130) are anticipated to be useful in the treatment of patients having cell damage to the selected cell populations in the same manner as is IL-11, and/or in combination with IL-11. See, N.Y. Ip et al., *Cell,* 69:1121–1132 (1992).

Another preferred cytokine for use in this invention shares common biological activities with IL-11 is Interleukin-6 (IL-6), which is described in detail in PCT patent application WO88/00206, published Jan. 14, 1988 and incorporated by reference herein.

Still another cytokine sharing the IL-11 signal transduction pathway is Leukemia Inhibitory Factor (LIF), also known as Cholinergic Differentiation Factor (CDF), and is described in detail in PCT patent application WO90/02183, published Mar. 8, 1990. Another cytokine characterized in this way is Oncostatin M (OSM), described in detail in European patent application No. 290,949, published Nov. 12, 1988. Additionally, Ciliary Neurotrophic Factor (CNTF) shares this signal transduction pathway, and is anticipated to be useful in the methods of restoring these cell populations. CNTF is described in detail in PCT patent application WO9104316, published Apr. 4, 1991.

It is further anticipated that other cytokines are likely to be useful in the methods of this invention, either in place of, or in combination with, IL-11, IL-6 and/or one or more of the above disclosed cytokines. One additional cytokine useful in a therapeutic method or combination pharmaceutical preparation according to this invention is Interleukin-1 (IL-1). IL-1 is described in detail in European patent application No. 456,332, published Nov. 13, 1991. Another useful cytokine is known as Natural Killer Cell Stimulatory Factor (NKSF), also termed Interleukin-12 (IL-12). This cytokine is described in detail in PCT patent application WO9205256, published Apr. 2, 1992.

Other cytokines which may be useful in these methods of restoring the cell populations selected from small intestinal epithelial cells, epithelial cells lining the large intestines and stomach, skin cells, hair cells, and sperm cells include Interleukin-3 (IL-3), and Granulocyte-Macrophage Colony Stimulating Factor (GM-CSF). GM-CSF is described in detail in PCT patent application WO8600639, published Jan. 30, 1986, [see, also, European Patent Application No. 281,069, published Sep. 7, 1988]. IL-3 is described in detail in U.S. Pat. No. 4,959,455, issued Sep. 25, 1990.

For additional general information on these cytokines, see also, F. Takatsuki et al., *Cancer Res.,* 50:2885–2890 (1990); D. P. Gearing et al., *Science,* 255:1434–1437 (1992); G. Damia et al., *Cancer Res.,* 52:4082–4089 (1992).

For use in the methods of treatment disclosed in this invention, the above-described cytokines or biologically active fragments thereof may be prepared by genetic engineering techniques, as disclosed in the above-incorporated references. Moreover, in addition to recombinant techniques, the cytokine polypeptides described above may also be produced by known conventional chemical synthesis. Methods for constructing the polypeptides useful in the present invention by synthetic means are known to those of skill in the art. The synthetically constructed cytokine polypeptide sequences, by virtue of sharing primary, secondary, or tertiary structural and conformational characteristics with the natural cytokine polypeptides are anticipated to possess biological activities in common therewith. Such synthetically constructed cytokine polypeptide sequences or fragments thereof which duplicate or partially duplicate the functionality thereof may also be used in the method of this invention. Thus, they may be employed as biologically active or immunological substitutes for the natural, purified cytokines useful in the present invention.

Modifications in the protein, peptide or DNA sequences of these cytokines or active fragments thereof may also produce proteins which may be employed in the methods of this invention. Such modified cytokines can be made by one skilled in the art using known techniques. Modifications of interest in the cytokine sequences, e.g., the IL-11 sequence, may include the replacement, insertion or deletion of one or more selected amino acid residues in the coding sequences. Mutagenic techniques for such replacement, insertion or deletion are well known to one skilled in the art. [See, e.g., U.S. Pat. No. 4,518,584].

Other specific mutations of the sequences of the cytokine polypeptides which may be useful therapeutically as described herein may involve, e.g., the insertion of one or more glycosylation sites. An asparagine-linked glycosylation recognition site can be inserted into the sequence by the deletion, substitution or addition of amino acids into the peptide sequence or nucleotides into the DNA sequence. Such changes may be made at any site of the molecule that is modified by addition of O-linked carbohydrate. Expression of such altered nucleotide or peptide sequences produces variants which may be glycosylated at those sites.

Additional analogs and derivatives of the sequence of the selected cytokine which would be expected to retain or prolong its activity in whole or in part, and which are expected to be useful in the present method, may also be easily made by one of skill in the art. One such modification may be the attachment of polyethylene glycol (PEG) onto existing lysine residues in the cytokine sequence or the insertion of one or more lysine residues or other amino acid residues that can react with PEG or PEG derivatives into the sequence by conventional techniques to enable the attachment of PEG moieties.

Additional analogs of these selected cytokines may also be characterized by allelic variations in the DNA sequences encoding them, or induced variations in the DNA sequences encoding them. It is anticipated that all analogs disclosed in the above-referenced publications, including those characterized by DNA sequences capable of hybridizing to the disclosed cytokine sequences under stringent hybridization conditions or non-stringent conditions [Sambrook et al, *Molecular Cloning. A Laboratory Manual*, 2d edit., Cold Spring Harbor Laboratory, New York (1989)] will be similarly useful in this invention.

Also considered useful in these methods are fusion molecules, prepared by fusing the sequence or a biologically active fragment of the sequence of one cytokine to another cytokine or proteinaceous therapeutic agent, e.g., IL-11 fused to IL-6 [see, e.g., methods for fusion described in PCT Patent Application No. WO92/04455, published Mar. 19, 1992, incorporated herein by reference]. Alternatively, combinations of the cytokines may be administered together according to the method.

Thus, where in the description of the methods of this invention a particular cytokine is mentioned by name, it is understood by those of skill in the art that the named cytokine encompasses the protein produced by the sequences presently disclosed in the art, e.g., for IL-11, the sequences of FIGS. 1 and 2, as well as proteins characterized by the modifications described above yet which retain substantially similar activity in restoring the cell populations of one or more of the cell populations identified herein.

The present invention thus involves treating patients having damaged or depleted cell populations selected from small intestinal epithelial cells, epithelial cells lining the large intestines and stomach, liver epithelial cells, skin cells, hair cells, and sperm cells. The treatment involves administering an effective amount of a selected cytokine in a pharmaceutical carrier. This treatment enables the restoration or regeneration of the damaged or depleted cell population primarily by the stimulation, direct or indirect, of any undamaged stem cells. The stem cells are stimulated to differentiate into the cell population which had been damaged or depleted.

Cytotoxic agents used in bone marrow transplantation and cancer therapy affect rapidly proliferating cells in both the bone marrow and small intestine, leading to severe and often dose-limiting toxicities. The present invention overcomes this problem as is exemplified below in the treatment of small intestinal epithelial cells (gut cells) damaged by chemotherapy or radiation therapy with IL-11 or IL-6 as the selected cytokine. In Examples 4–9, analysis of small intestinal mucosa demonstrated rapid recovery of villi length and increased proliferative activity within the crypt cells of IL-11-treated or IL-6-treated mice compared to control mice. For example, in these examples, with mice, IL-11 and/or IL-6 had a positive effect on mouse survival after exposure to 5-fluorouracil and irradiation without an effect on peripheral neutrophil (white blood cell) counts. Further, these studies provided evidence of rapid recovery of the small intestinal mucosa. Thus, IL-11 and IL-6 have positive effects on the recovery of several tissues where dose-limiting toxicities following cytoablative therapies occur.

Where damage to, or depletion of, gut cells or other cell populations is caused by therapy, the treatment of the present invention may occur simultaneously with, or sequentially after, the therapy, e.g., chemotherapy or radiation. For example, effective amounts of IL-11 alone, IL-6 alone, another cytokine alone, or a combination of cytokines, may be administered in a suitable pharmaceutical carrier.

Preferably, treatment begins concurrently with or shortly after the chemotherapy or radiation therapy is begun and is continued until the level of the gut cells or other cells is returned to acceptable levels. However, the selected cytokine, e.g., IL-11, IL-6, or combination of cytokines, may be administered for a suitable period of time prior to the beginning of chemotherapy or radiation therapy to improve the efficacy with which the cytokine, e.g., IL-11, IL-6, stimulates the stem cell which differentiates into the mature gut cell.

The invention also involves methods for treating patients afflicted with damaged or depleted cell populations selected from small intestinal epithelial cells, epithelial cells lining the large intestines and stomach, liver epithelial cells, skin cells, hair cells, and sperm cells, where the damage or depletion is caused by autoimmune disease. For example, Crohn's disease, damages and depletes the population of normally rapidly dividing gut cells. Other autoimmune diseases may similarly affect the cells of the large intestine or stomach, liver, skin and hair, and sperm cells. The present invention also involves treating such conditions by administering effective doses of a selected cytokine, e.g., IL-11, IL-6, or combination of cytokines.

Similarly, infection, trauma or shock can damage or deplete normal populations of gut cells, as well as the other cells mentioned herein, thereby requiring the administration of effective amounts of one or more cytokines, particularly IL-11 or IL-6.

In one embodiment of the present invention, a selected cytokine, IL-11 or IL-6, obtained by recombinant expression or prepared synthetically and purified to homogeneity, is combined with a pharmaceutical carrier suitable for internal administration. Purification is performed using conventional techniques (see, e.g., PCT/US90/06803 and the examples below).

Suitable pharmaceutically acceptable carriers facilitate administration of the cytokine, e.g., IL-11, IL-6, and are well known in the art. Exemplary carriers include sterile saline, lactose, sucrose, calcium phosphate, gelatin, dextrin, agar, pectin, peanut oil, olive oil, sesame oil, and water. Additionally, the carrier or diluent includes a time delay material, such as glyceryl monostearate or glyceryl distearate alone or with a wax. In addition, slow release polymer formulations can be used. Suitable sustain-release matrices contain the active ingredient in a mixture with one or more of the following: sodium bentonite, ethylcellulose, stearic acid, calcium stearate, adipic acid, fumeric acid, polyethylene glycol, deacetylated chitin, and cellulose acetate. Suitable preservatives and/or stabilizers may be included.

Alternatively, the selected cytokine, e.g., IL-11, IL-6, or others mentioned herein, can be combined with other conventional agents useful in alleviating the symptoms associated with chemotherapy, such as antiemetics, anti-oxidants, and other hematopoietic growth factors.

The therapeutic method of the present invention may also include co-administration or combination of a selected cytokine with other human factors known to those of skill in the art. Exemplary cytokines or hematopoietins for such use include those cytokines specifically referenced above. Growth factors, such as B cell growth factor, B cell differentiation factor, or eosinophil differentiation factors may also prove useful in co-administration with these cytokines. Other agents for co-administration may include other pharmaceutically effective chemical agents and drugs, e.g., such as agents to control infection. The dosage recited below would be adjusted to compensate for such additional components in the therapeutic composition. Progress of the treated patient can be monitored by conventional methods.

Without wishing to be bound by theory, the inventors believe that treatment of damage to, or depletion of, the normally rapidly dividing gut epithelial cells with IL-11, IL-6 or another cytokine, provides two important advantages to current methods of dealing with gut toxicity. First, the cytokine, e.g., IL-11 and/or IL-6, improves the integrity of the gut by stimulating the stem cells to restore a healthy cell population, thereby preventing entry of bacteria and fungi into the blood of the treated patient. IL-11, IL-6 or other mentioned cytokine treatment of patients can thereby reduce the morbidity and mortality associated with chemotherapy and radiation treatment-induced gut damage. Additionally, IL-11 and/or IL-6 and/or other cytokines herein mentioned may allow increased amounts of chemotherapy and radiation therapy to be used in cancer treatments, a highly desirable effect, since this may improve the survival rates of patients with certain cancers which are currently fatal.

Similarly, in the treatment of autoimmune diseases of the small intestine, a cytokine, such as IL-11, IL-6 and others, is expected to restore the cell population thereby improving healing and reducing morbidity and mortality without the deleterious side effects of previous therapies.

The treatment of a patient with a selected cytokine, such as IL-11, IL-6, or a combination of cytokines is anticipated to have the same effects on other cell populations, e.g., skin, hair, sperm cells, epithelial linings of stomach and large intestines, and liver epithelial cells, which are damaged or depleted by disease, infection, shock or trauma. The cytokine is theorized to restore healthy populations by stimulating stem cells into differentiating into mature cell populations.

In the treatment of any of these conditions resulting in damage to, or depletion of, the cell population, the cytokine, e.g., IL-11, IL-6, or others, can be administered by any suitable route, but is preferably administered systemically, i.e., parenterally. Of the parental routes, subcutaneous and intraperitoneal are preferred. With chemotherapy, intravenous administration may be desired.

A suitable treatment regimen for patients undergoing chemotherapy or radiation, or for patients who have already sustained cell damage or depletion due to trauma or disease, may be determined by the attending physician based upon such factors as the patient's age, sex, weight, and general health. Generally, a suitable dose of a cytokine, e.g., IL-11, ranges between about 1 $\mu$g/kg body weight and about 1000 $\mu$g/kg body weight. If desirable, these doses can be adjusted to units. A unit is conventionally described as the concentration of polypeptide which leads to half maximal stimulation in a suitable assay, e.g., for IL-11, the T1165 assay described in PCT/US90/06803. Another suitable dose may be in the range of between about 10 $\mu$g/kg and about 1000 $\mu$g/kg, and more preferably about 100 $\mu$g/kg and about 500 $\mu$g/kg, of cytokine, e.g., IL-11, per kg of body weight. These doses may be administered daily for between 1 day and 6 months, or for as long as is deemed necessary, depending on the nature of the cell damage or depletion.

The dosages of the other cytokines described herein may be similar or adjusted downwardly depending on the toxicity of the selected cytokine. For example, IL-1 would be administered in a dosage range of about 10 ng/kg body weight to about 1 $\mu$g/kg body weight due to its toxicity. The adjustment of the dosages is well within the skill of the art based on the known toxicities of the cytokines useful in this invention.

When used to treat autoimmune conditions, the cytokine composition, e.g., IL-11, may be formulated to contain other agents useful in alleviating the symptoms of these conditions, including e.g., prednisone, cyclosporine, cyclophosphamide, and azathioprine, as well as other known agents.

Also, where treatment is directed to skin and hair cells, a pharmaceutical preparation may be prepared using agents which are conventional for topically administering therapeutics to the skin and hair, e.g., for systemic or local or topical administration. Suitable pharmaceutical carriers for a topical composition of the present invention may include several conventional ingredients of creams, lotions, gels or ointments. Such conventional ingredients are included in skin creams or oils for topical administration for treating a variety of diseases of the skin. Such compositions may be used as drug delivery systems to transmit the IL-11 through the skin or to facilitate the absorption of the IL-11 into the skin or onto a rash or other skin eruption. [See, e.g., U.S. Pat. No. 3,981,996; U.S. Pat. No. 4,731,241; U.S. Pat. No. 4,164,563; U.S. Pat. No. 3,924,004; U.S. Pat. No. 3,888,995; U.S. Pat. No. 3,592,930; and U.S. Pat. No. 4,753,958].

The following examples illustrate the methods of the present invention employing IL-11 as the selected cytokine, and gut cell populations damaged and depleted by chemotherapy as the model rapidly growing cell population. However, these examples do not limit the scope of the invention.

EXAMPLE 1—HUMAN IL-11

The isolation and cloning of human IL-11 is described in detail in published PCT Application No.

US90/06803 and now known to the art. The full sequence for human IL-11 was determined and is shown in FIG. 1 below. This protein is characterized by the sequence of FIG. 1 [SEQ ID NO:1 and 2]. These descriptions are incorporated by reference herein.

EXAMPLE 2—THIOREDOXIN-IL-11 FUSION MOLECULE

IL-11 was also prepared in a fusion molecule for use in the method of the present invention. The fusion molecule contained E. coli thioredoxin and recombinant IL-11, obtained as described in PCT Application No. US90/06803 incorporated by reference [see also Paul et al, *Proc. Natl. Acad. Sci. U.S.A.*, 87:7512-7516 (1990) and PCT Patent publication WO91/07495, published May 30, 1991 incorporated herein by reference].

The E. coli thioredoxin (trxA) gene was cloned based on its published sequence [Lim et al, *J. Bacteriol.*, 163:311-316 (1985)] and employed to construct various related E. coli expression plasmids using standard DNA manipulation techniques, described extensively by Sambrook, Fritsch and Maniatis, *Molecular Cloning. A Laboratory Manual*, 2nd edition, Cold Spring Harbor Laboratory, Cold Spring Harbor, N.Y. (1989). (Nucleotides 2242-2568 of FIG. 2 encode the E. coli thioredoxin protein.)

An expression plasmid pALtrxA-781 was constructed containing the E. coli trxA gene without fusion to another sequence. This plasmid, which directs the accumulation of >10% of the total cell protein as thioredoxin in an E. coli host strain GI724, was further manipulated to provide for the construction of a trxA/IL-11 fusion sequence, resulting in the expression vector, pALtrxA/EK/IL-11ΔPro-581.

The entire sequence of the plasmid expression vector, pALtrxA/EK/IL-11ΔPro-581 [SEQ ID NO:3 and SEQ ID NO:4], is illustrated in FIG. 2 and contains the following principal features:

Nucleotides 1-2060 contain DNA sequences originating from the plasmid pUC-18 [Norrander et al, *Gene*, 26: 101-106 (1983)] including sequences containing the gene for β-lactamase which confers resistance to the antibiotic ampicillin in host E. coli strains, and a colE1-derived origin of replication. Nucleotides 2061-2221 contain DNA sequences for the major leftward promoter (pL) of bacteriophage λ [Sanger et al, *J. Mol. Biol.*, 162:729-773 (1982)], including three operator sequences, $O_L1$, $O_L2$, and $O_L3$. The operators are the binding sites for λcI repressor protein, intracellular levels of which control the amount of transcription initiation from pL. Nucleotides 2222-2241 contain a strong ribosome binding sequence derived from that of gene 10 of bacteriophage T7 [Dunn and Studier, *J. Mol. Biol.*, 166:477-535 (1983)].

Nucleotides 2242-2568 contain a DNA sequence encoding the E. coli thioredoxin protein [Lim et al, *J. Bacteriol.*, 163:311-316 (1985)]. There is no translation termination codon at the end of the thioredoxin coding sequence in this plasmid.

Nucleotides 2569-2583 (SEQ ID NO:3 and SEQ ID NO:4) contain a DNA sequence encoding the amino acid sequence for a short, hydrophilic, flexible spacer peptide "—GSGSG—". Nucleotides 2584-2598 provide DNA sequence encoding the amino acid sequence for the cleavage recognition site of enterokinase (EC 3.4.4.8), "—DDDDK—" [Maroux et al, *J. Biol. Chem.*, 246:5031-5039 (1971)].

Nucleotides 2599-3132 contain a DNA sequence encoding the amino acid sequence of a modified form of mature human IL-11 [Paul et al, *Proc. Natl. Acad. Sci. USA*, 87:7512-7516 (1990)]; the N-terminal prolyl-residue normally found in the natural protein has been deleted. Thus, these nucleotides encode IL-11 beginning with amino acid #2 of the mature native sequence. The sequence includes a translation termination codon at the 3'-end of the IL-11 sequence.

Nucleotides 3133-3159 provide a "Linker" DNA sequence containing restriction endonuclease sites. Nucleotides 3160-3232 provide a transcription termination sequence based on that of the E. coli aspA gene [Takagi et al, *Nucl. Acids Res.*, 13:2063-2074 (1985)]. Nucleotides 3233-3632 are DNA sequences derived from pUC-18.

As described in Example 3 below, when cultured under the appropriate conditions in a suitable E. coli host strain, can direct the production of high levels (approximately 10% of the total cellular protein) of a thioredoxin-IL-11 fusion protein. By contrast, when not fused to thioredoxin, IL-11 accumulated to only 0.2% of the total cellular protein when expressed in an analogous host/vector system.

EXAMPLE 3—EXPRESSION OF A FUSION PROTEIN

A thioredoxin-IL-11 fusion protein was produced according to the following protocol using the plasmid constructed as described in Example 2. pALtrxA/EK/IL-11ΔPro-581 (SEQ ID NO: 3) was transformed into the E. coli host strain GI724 (F−, lacI$^q$, lacP$^{L8}$, ampC::-λcI+) by the procedure of Dagert and Ehrlich, *Gene*, 6: 23 (1979). The untransformed host strain E. coli GI724 was deposited with the American Type Culture Collection, 12301 Parklawn Drive, Rockville, Md. on Jan. 31, 1991 under ATCC No. 55151 for patent purposes pursuant to applicable laws and regulations. Transformants were selected on 1.5% w/v agar plates containing IMC medium, which is composed of M9 medium [Miller, "Experiments in Molecular Genetics", Cold Spring Harbor Laboratory, New York (1972)] supplemented with 0.5% w/v glucose, 0.2% w/v casamino acids and 100 μg/ml ampicillin.

GI724 contains a copy of the wild-type λcI repressor gene stably integrated into the chromosome at the ampC locus, where it has been placed under the transcriptional control of *Salmonella typhimurium* trp promoter/operator sequences. In GI724, λcI protein is made only during growth in tryptophan-free media, such as minimal media or a minimal medium supplemented with casamino acids such as IMC, described above. Addition of tryptophan to a culture of GI724 will repress the trp promoter and turn off synthesis of λcI, gradually causing the induction of transcription from pL promoters if they are present in the cell.

GI724 transformed with pALtrxA/EK/IL-11ΔPro-581 [SEQ ID NO:3 and SEQ ID NO:4] was grown at 37° C. to an $A_{550}$ of 0.5 in IMC medium. Tryptophan was added to a final concentration of 100 μg/ml and the culture incubated for a further 4 hours. During this time thioredoxin-IL-11 fusion protein accumulated to approximately 10% of the total cell protein.

All of the fusion protein was found to be in the soluble cellular fraction, and was purified as follows. Cells were lysed in a French pressure cell at 20,000 psi in 50 mM HEPES pH 8.0, 1 mM phenylmethylsulfonyl fluoride. The lysate was clarified by centrifugation at 15,000×g for 30 minutes and the supernatant loaded onto a QAE-Toyopearl column. The flow-through fractions were discarded and the fusion protein eluted with 50 mM HEPES pH 8.0, 100 mM NaCl. The eluate was adjusted to 2M NaCl and loaded onto a column of phenyl-Toyopearl. The flow-through fractions were again discarded and the fusion protein eluted with 50 mM HEPES pH 8.0, 0.5M NaCl.

The fusion protein was then dialyzed against 25 mM HEPES pH 8.0 and was >80% pure at this stage. By T1165 bioassay [Paul et al, cited above], the purified thioredoxin-IL-11 protein exhibited an activity of $8 \times 10^5$ U/mg. This value agrees closely on a molar basis with the activity of $2 \times 10^6$ U/mg found for COS cell-derived IL-11 in the same assay. One milligram of the fusion protein was cleaved at 37° C. for 20 hours with 1000 units of bovine enterokinase [Leipnieks and Light, *J. Biol. Chem.*, 254:1677–1683 (1979)] in 1 ml 10mM Tris-Cl (pH 8.0)/10mM $CaCl_2$. IL-11 could be recovered from the reaction products by passing them over a QAE-Toyopearl column in 25 mM HEPES pH 8.0, where IL-11 was found in the flow-through fractions. Uncleaved fusion protein, thioredoxin and enterokinase remained bound on the column.

EXAMPLE 4—TREATMENT OF IRRADIATED MICE

The IL-11 used in the tests below was obtained from Genetics Institute, Inc., Cambridge, Mass. and was prepared in *E. coli* essentially as described in the examples above. The IL-11 (140 μg/ml) was then mixed with 10 mM Tris buffer, to a pH of about 8.0. The level of endotoxin in this in vivo grade formulation is about 1.4 U/mg of protein. The preparation also contains about 10% molar hydroxylmate and about 3 ng/ml (0.002%) thioredoxin.

Eight-ten week old C3H/HeJ [Jackson Labs] mice were administered intraperitoneally (i.p.) 150 mg/kg 5-fluorouracil (5-FU) diluted in Hanks Balanced Salt Solution (HBSS) containing 0.024M Hepes buffer [both Gibco], three days prior to sublethal irradiation. Irradiation consisted of 6.0 Gys TBI delivered by Siemens 250 Kvp X-ray therapy machine, filtered with 1.0 mm Cu, giving half value layer of 2.1 mm Cu at 50 cm SSD, and with a dose rate of 78.13 (cGy/min). On the same day as the irradiation dose was given, mice were administered the above-described recombinant in vivo grade human IL-11 [Genetics Institute] at a divided dose (twice/day) of 250 micrograms/kg/day. These divided doses were given in 0.2 ml volumes subcutaneously in HBSS with Hepes and 0.1% bovine serum albumin (BSA) [Boehringer-Mannheim]. Control animals received the same volume of HBSS and BSA without IL-11. Treatment was continued for 9 to 18 days post-irradiation or until animals died.

Hematologic analysis of leukocyte cell counts and platelet counts were performed on tail vein bleeds on a Coulter Counter Model ZM [Coulter Electronics] using a 100 micron aperture for leukocyte determinations and a 50 micron aperture for platelet determinations. Red blood cells were lysed using Zapglobin [Coulter] according to manufacturer's recommendations. Blood smears were stained with Wright-Giemsa using standard methods and examined at 100× for differential analysis. The absolute numbers of neutrophils, lymphocytes, monocytes, and eosinophils in the peripheral blood was calculated by multiplying the total leukocyte counts with the percentage of leukocytes obtained on the differential. Peripheral blood hematocrits were performed by spinning capillary tubes for five minutes in a Clay-Adams hematocrit centrifuge.

Whole dead mice (dying in the course of the experiment or by sacrifice) were fixed in 10% buffered formalin overnight. One femur/mouse was fixed in Bouin's solution. Tissues from each organ (liver, spleen, kidney, small intestine mesentery, abdominal wall, lung, heart, testes, and femur) were embedded in paraffin wax using standard techniques and four micron sections were cut and stained with hematoxylin and eosin. For analysis of small intestinal crypts, ten independent measurements of villus height, crypt depth, and metaphases/crypt were made in each section of small intestine using an objective-mounted micrometer.

Results are expressed in Table I below as the mean +/− SD unless otherwise stated. The probability of significant differences when two related groups were compared was determined using a two-tailed Student t-test. The probability of significant differences when multiple treatments were examined was determined by analysis of variance followed by Student-Newman-Keuls multiple range tests to define the unique subsets within the study.

TABLE I

Effect of IL-11 on Endogenous Infection Combined Modality Model

| Mouse No. | Day Post-Irradiat. Examined[1] | Diarrhea[2] | Hepatic Bacterial Foci Macroscopic[3] | Hepatic Bacterial Foci Microscopic[4] |
|---|---|---|---|---|
| BSA | | | | |
| 1 | 5 | + | 0 | +++ |
| 2 | 8 | − | 19 | ++ |
| 3 | 5 | + | 21 | +++ |
| 4 | 6 | − | 79 | +++ |
| 5 | 9 | − | 119 | +++ |
| IL-11 | | | | |
| 1 | 9 | + | 0 | + |
| 2 | 4 | + | 0 | − |
| 3 | 9 | − | 14 | ++ |
| 4 | 9 | − | 3 | + |
| 5 | 9 | − | 0 | − |

[1]All animals sacrificed at day 9, other days represent day of death.
[2]+ = present at day of death
− = no diarrhea
[3]Surface foci present on fixed liver.
[4]Microscopic foci present on examination of randomly chosen histologic sections; + <10 foci/section; ++ 10–50; +++ >50.

In three separate experiments, all control mice died between day 3 and day 10 after irradiation, while only 3/13 (23%) of IL-11 treated mice died (on days 4, 9, 10 post-irradiation). In experiment 1, all control animals died by day 9. Animals were autopsied on the day of death or (in the treated group) on day 9 by sacrificing remaining animals (day of examination listed in Table I). At autopsy, 4/5 mice in the control group had macroscopic infection foci in the liver compared to 2/5 of the IL-11 treated mice. In addition, the foci present in IL-11 treated mice were present in fewer numbers and smaller in size (Table I). These foci subsequently were demonstrated to contain *E. coli* bacteria by identification using microbiological analysis. Microscopically many foci (12–129/random section) were found within the liver from control mice, while fewer (6–21/section) were demonstrated in IL-11 treated mice (Table I). Similar bacterial foci were also seen in the mesentery and spleen of animals.

Surprisingly, these differences in mortality and the presence of bacterial foci in organs of mice were not associated with differences in peripheral leukocyte counts or absolute neutrophil counts as shown by data in Table II.

TABLE II

Effect of rhIL-11 on Peripheral Blood Counts in Mice Combined Modality Model

| Day[1] | Treatment | WBC × $10^3$/mm$^3$ | Platelet $10^3$/mm$^3$ |
|---|---|---|---|
| Day 1 | BSA | 5.56 ± 1.80(5) | 894.7 ± 168.3(5) |
|  | IL-11 | 4.89 ± 0.16(5) | 770.3 ± 192.6(5) |
| Day 3 | BSA | 0.49 ± 0.16(10) | 294.8 ± 43.1(10) |
|  | IL-11 | 0.64 ± 0.31(10) | 454.1 ± 115.5(10) |
| Day 4 | BSA | 0.43 ± 0.04(10) | 237.4 ± 109.6(10) |
|  | IL-11 | 0.49 ± 0.14(10) | 337.3 ± 143.2(10) |
| Day 5 | BSA | 0.30 ± 0.06(9) | 126.6 ± 55.1(10) |
|  | IL-11 | 0.31 ± 0.07(11) | 171.9 ± 76.9(11) |
| Day 6 | BSA | 0.40 ± 0.24(9) | 134.4 ± 80.7(9) |
|  | IL-11 | 0.47 ± 0.22(12) | 257.9 ± 195.2(12) |
| Day 8 | BSA | 1.19 ± 0.13(2) | 236.1 ± 18.2(2) |
|  | IL-11 | 0.72 ± 0.23(7) | 365.6 ± 256.1(7) |
| Day 9 | BSA | 1.39 ± 0.32(2) | 269.0 ± 100.8(2) |
|  | IL-11 | 1.06 ± 0.45(9) | 248.8 ± 92.4(9) |

[1]Post-irradiation
( ) number of animals
*$p < 0.001$ compared to BSA group

Since *E. coli* are a known resident organism of the small intestine, the increase in bacterial infection and mortality in the control animals probably reflects gut toxicity from irradiation and chemotherapy. Histologic section of the small intestine and morphometric quantitation of the length of the small intestine villi confirmed extensive damage in control mice as shown by data in Tables IIIA and IIIB. In contrast, IL-11 treatment was associated with almost complete preservation of villi length (Table IIIA). In addition, IL-11 treated mice demonstrated near normal numbers of mitotic crypt cells, a further indication of stimulation of proliferation of crypt progenitor or stem cells.

TABLE IIIA

Effect of IL-11 of Murine Gut Epithelium Combined Modality Mode

|  | C Crypt Depth[1] | V Villi Length | C (C/C + V) × 100% |
|---|---|---|---|
| Normal (2) | 84.1 ± 21.1 | 477.7 ± 99.8 | 15.4 ± 5.9 |
| Day 5 |  |  |  |
| BSA(5) | 122.8 ± 29.5 | 253.7 ± 79.7 | 33.5 ± 8.2 |
| IL-11(5) | 117.1 ± 14.5 | 512.8 ± 6.7** | 19.5 ± 6.7** |
| Day 9 |  |  |  |
| BSA(2) | 124.6 ± 40.7 | 330.1 ± 92.1 | 27.3 ± 1.0 |
| IL-11(2) | 98.5 ± 7.0 | 405.9 ± 84.3 | 19.9 ± 4.4 |

( ) number of animals
[1] = in microns
* = $p < 0.01$ compared to BSA group
** = $p < 0.02$ compared to BSA group

TABLE IIIB

Effect of IL-11 of Murine Gut Epithelium Combined Modality Mode

|  | Crypt Cir. | Mitoses/ Crypt | Mitoses/ 100μ crypt |
|---|---|---|---|
| Normal (2) | 162.3 ± 11.6 | 1.8 ± 0.4 | 1.07 ± 0.14 |
| Day 5 |  |  |  |
| BSA(5) | 853.4 ± 62.2 | 0.9 ± 0.4 | 0.10 ± 0.04 |
| IL-11(5) | 928.2 ± 104.4 | 2.0 ± 0.5* | 0.22 ± 0.06* |
| Day 9 |  |  |  |
| BSA(2) | 830.0 ± 28.2 | 1.1 ± 0 | 0.13 ± 0 |
| IL-11(2) | 957.5 ± 10.4 | 2.2 ± 0.6 | 0.23 ± 0.06 |

( ) number of animals
[1] = in microns
* = $p < 0.01$ compared to BSA group
** = $p < 0.02$ compared to BSA group These data demonstrate that the administration of IL-11 in vivo has marked positive effects on the recovery of small intestinal crypt epithelial cells from the combined cytotoxic effects of radiation and chemotherapy.

EXAMPLE 5—SURVIVAL OF MICE FOLLOWING COMBINED CHEMOTHERAPY/RADIATION

Eight-ten week old C3H/HeJ mice [Jackson Laboratory, Bar Harbor, Me.] were given 5-fluorouracil (5-FU) (diluted in Hanks Balanced Salt Solution (HBSS) containing 0.025M Hepes) [G. R. Siber et al, *Cancer Res.*, 40, 3430–3436 (1980)] at 150 mg/kg body weight I.P. three days prior to sublethal irradiation (6.0 Gys total body irradiation delivered from a Siemens 250 KVp X-ray therapy machine, filtered with 1.0 mm Cu, giving a half value layer of 2.1 mm Cu at 50 cm SSD, and with a dose rate of 78.13 cGy/min). No bone marrow infusions were given to these animals.

Recombinant human IL-11 (rhIL-11) [provided by Genetics Institute, Cambridge, Mass. and prepared in *E. coli* essentially as described in th examples above] was diluted in HBSS [HBSS-Gibco] containing 0.1% BSA [wt/vol, Boehringer-Mannheim, Indianapolis, Ind.] and 0.025M Hepes [Gibco]. RhIL-11 (250 micrograms/kg body weight) was injected subcutaneously in 0.2 ml volumes twice per day starting on the same day as irradiation. Control mice received the same volume of HBSS/0.1% BSA (vehicle injections).

Following treatment with 5-FU and sublethal doses of X-irradiation (combined modality, CM, therapy), damage to the small intestine of C3H/HeJ mice is extensive and the majority of mice die within 10 days. Dying animals demonstrate wasting, diarrhea, and tilting and rotating indicative of central nervous system infection. Treatment of mice with 250 micrograms/kg/day of recombinant human interleukin-11 (rhIL-11) was associated with significant increase in survival following this cytoablative therapy, in spite of no increase in peripheral neutrophil counts or bone marrow myeloid progenitors.

Additional experiments in which increasing doses and an alternative source of irradiation ($^{137}$Cs) were administered confirmed the increase in survival in IL-11 treated mice over several dose ranges. The experiments tested radiation doses of 6.0, 7.0, 7.5 and 8.0 Gy (using $^{137}$CS source at 95.83 cGy/min) as above (all following 150 mg/kg 5-FU) and included a total of 135 mice. Survival in the control group in all experiments was 27% compared to 62% in the IL-11 treated mice ($p<0.0001$). IL-11 treatment was associated with a marked reduction in the number of bacterial foci in multiple organs with none detectable in many mice after sacrifice. Microbiological analysis of foci dissected from the liver of control mice uniformly demonstrated that the causative organism was *E. coli*, a common enteric organism in mice.

EXAMPLE 6—HISTOLOGIC SECTIONS OF SMALL INTESTINE

To determine the potential source of *E. coli* organisms demonstrated in mice following CM treatment, histologic sections of the small intestine were examined in control and IL-11 treated mice sacrificed daily after irradiation.

Mice dying or sacrificed following the combined radiation/chemotherapy (as described in Example 5 above) were autopsied and tissues fixed in 10% buffered formalin overnight within 12 hours after death. Tissues from each organ (liver, spleen, kidney, small intestine and mesentery, abdominal wall, lung, heart, and femurs) were embedded in paraffin wax using standard techniques. Four-micron sections were cut and stained with hematoxylin/eosin (H&E). Ten independent measurements of villus height, crypt depth and metaphases/crypt per specimen of small intestine were made from mice sacrificed daily using an objective mounted micrometer at 200× magnification. Hepatic bacterial foci were counted both macroscopically as surface colonies and microscopically on randomly chosen liver histologic sections.

The small intestinal mucosa of control mice showed marked destruction of villus structure with shortening of the villus length, vacuolization, and pyknotic nuclear structures. In contrast, IL-11 treated mice demonstrated mild changes in morphology of the small intestinal villi. Morphometric analysis of crypt and villi length demonstrated a significant increase in the ratio of the crypt depth/villi length in IL-11 treated mice compared to control mice (Table IV below). Villus shortening was most prominent 24 hours after irradiation in both groups of mice, while remaining abnormal in surviving control mice through day 9.

TABLE IV

Effect of IL-11 on Small Intestine Crypt Cell Recovery Post 5-FU and Irradiation

| | CRYPT DEPTH | | VILLUS LENGTH | |
|---|---|---|---|---|
| | BSA | IL-11 | BSA | IL-11 |
| Day 1 | 76.8 ± 9.2 | 71.1 ± 4.7 | 398.6 ± 45.5 | 479.0 ± 31.8 |
| Day 2 | 123.4 ± 14.3 | 129.0 ± 7.8 | 491.9 ± 23.2 | 603.4 ± 41.9[2] |
| Day 3 | 154.5 ± 10.2 | 141.8 ± 19.9 | 468.7 ± 47.4 | 533.9 ± 24.2 |
| Day 4 | 141.5 ± 11.9 | 118.5 ± 14.0 | 500.2 ± 51.3 | 635.0 ± 26.9[2] |
| Day 5 | 120.6 ± 11.7 | 117.8 ± 7.7 | 523.2 ± 17.4 | 661.5 ± 20.1[1] |

| | CRYPT/VILLUS | |
|---|---|---|
| | BSA | IL-11 |
| Day 1 | 0.20 ± 0.01 | 0.15 ± 0.00[1] |
| Day 2 | 0.25 ± 0.01 | 0.22 ± 0.00[2] |
| Day 3 | 0.33 ± 0.01 | 0.27 ± 0.01[1] |
| Day 4 | 0.29 ± 0.00 | 0.19 ± 0.00[1] |
| Day 5 | 0.23 ± 0.00 | 0.18 ± 0.01[1] |

[1] $p < 0.01$ vs BSA group
[2] $p < 0.05$ vs BSA group
Each number represents data from 3 animals
10 crypts/animal, 10 villi/animal

EXAMPLE 7—USE OF IL-11 OR IL-6 IN CYTOABLATIVE THERAPY

In an additional experiment, recombinant human IL-6 [Preprotech, Rocky Hill, N.J.] was diluted in HBSS [HBSS-Gibco] containing 0.1% BSA (wt/vol) and 0.025M HEPES. Ten C3H/HeJ mice were injected subcutaneously with recombinant human IL-6 (250 μg/kg body weight) in 0.2 mL volumes twice per day starting on the same day as irradiation.

Ten (10) mice were injected with 250 μg/kg body weight IL-11, as described in Example 5 above. Control mice (55) received the same volume of HBSS/0.1% BSA. The results of this study are provided in Table V below.

TABLE V

| | Percent Survival | | | | | | | | | | |
|---|---|---|---|---|---|---|---|---|---|---|---|
| Day | 2 | 4 | 5 | 6 | 7 | 8 | 9 | 10 | 11 | 12 | 13 |
| BSA: | 100 | 98 | 95 | 76 | 55 | 47 | 42 | 34 | 32 | 32 | 31 |
| IL11: | 90 | 90 | 90 | 90 | 80 | 80 | 80 | 80 | 80 | 70 | 70 |
| IL6: | 100 | 100 | 100 | 100 | 100 | 80 | 80 | 80 | 80 | 80 | 80 |

Treatment of mice with 500 μg/kg/day of recombinant human interleukin-6 resulted in significant increase in survival following this cytoablative therapy.

EXAMPLE 8—PCNA STAINING OF SMALL INTESTINAL CRYPTS

Since the villus length is dependent on proliferation and differentiation of crypt stem and progenitor cells [Chwalinski et al, *Am J. Anal.*, 186, 397–406 (1989); Ijiri, et al, *Br. J. Cancer*, 47, 175–185 (1983); Al-Dewachi, et al, *Cell Tissue Kinet.*, 10, 203–213 (1977)], the mitotic index of crypt cells was determined in control and IL-11 treated mice sacrificed daily after irradiation.

Proliferating cell nuclear antigen (PCNA) immunohistochemical staining was done on 2 cm jejunum sections obtained from CM mice sacrificed daily from day 1 to day 5 post irradiation (day 4–8 post 5-FU). Tissue was fixed in 10% formalin for 6–12 hours, paraffin-embedded, and sections were dried on polylysine-treated glass slides. Slides were then deparaffinized and rehydrated. Endogenous peroxidase was quenched by a 5 minute incubation in 3% hydrogen peroxide. The slides were covered with normal goat serum for 20 minutes, incubated overnight at 4° C. with PC10 antibody against PCNA [1:80 Dako, Santa Barbara, Calif.] and then stained for 30 minutes with a biotin-conjugated goat anti-mouse antibody [Gaithersburg, Md.], followed by peroxidase-conjugated streptavidin [both Kirkegaard & Perry Laboratories, Gaithersburg, Md.] for 30 minutes. The enzyme was developed with 3,3'-diaminobenzidine [DAB Sigma, St. Louis, Mo,]. PCNA positive nuclei stained brown. The percentage of PCNA positive crypt cells and absolute number of PCNA positive cells per crypt were measured by counting 20 randomly chosen crypts/sections/mouse.

TABLE VI

Effect of IL-11 on Proliferation of Small Intestine Crypt Cells as Quantitated by PCNA Staining

| | BSA | | IL-11 | |
|---|---|---|---|---|
| | + nuclei (%) | + nuclei/crypt (%) | + nuclei (%) | + nuclei/crypt (%) |
| Day 1 | 17.0 ± 6.8 | 3.1 ± 1.4 | 18.4 ± 9.2 | 5.0 ± 1.2 |
| Day 2 | 1.9 ± 1.3 | 0.4 ± 0.3 | 10.5 ± 1.0[1] | 2.6 ± 0.3[1] |
| Day 3 | 2.4 ± 1.7 | 0.8 ± 0.5 | 7.6 ± 1.9[2] | 2.1 ± 0.5[2] |
| Day 4 | 1.3 ± 0.4 | 0.4 ± 0.2 | 4.2 ± 1.5[2] | 1.3 ± 0.4[2] |
| Day 5 | 1.7 ± 0.4 | 0.6 ± 0.1 | 10.5 ± 11.3 | 3.3 ± 3.4 |

[1] $p < 0.01$ vs BSA group
[2] $p < 0.05$ vs BSA group
Each number represents data from 3 animals
20 crypts/animal, 400-600 nuclei Significant increases in the number of mitoses/crypt (2.0+/−0.5 vs 0.9+/−0.4, IL-11 vs control, $p<0.001$) as well as in the number of mitoses/100 micron of epithelial basement membrane (0.22+/−0.06 vs 0.10+/−0.04, $p<0.01$) were seen on day 5 after irradiation in the IL-11 treated mice. Control mice surviving to day 9 post irradiation demonstrated slightly increased numbers of mitotic crypt cells, but the numbers were still depressed compared to normal or IL-11 treated mice.

The increase in cell cycle activity following CM treatment and IL-11 administration was further characterized by staining with PC-10 [Hall, et al, *J. Pathol.*, 162, 285–294 (1990); Zeymer et al, *Am. J. Pathol.*, 141, 685–690 (1992); Garcia et al, *Am. J. Pathol.*, 134, 733–739 (1989)]. PC-10 is a monoclonal antibody directed against proliferating cell nuclear antigen (PCNA) and a member of the cyclin family of nuclear proteins (Table VI). IL-11 administration was associated with a 2 to 5-fold increase in the number of crypt cell nuclei staining with PC-10 on days 2–4 following irradiation. Taken together, these data demonstrate that IL-11 administration to mice following severe damage to the small intestinal crypt cells hastens recovery of the villus structure due to increased proliferation of presumably the crypt progenitor cell.

EXAMPLE 9—EFFECT OF IL-11 ON PROLIFERATION OF IEC-6 CELLS

In an effort to determine if the effect of IL-11 on the recovery of small intestinal villi seen in vivo was a direct effect of IL-11 on crypt progenitor cells, IEC-6 cells [Barnard, et al, *Proc. Natl. Acad. Sci., USA*, 86, 1578–1582 (1989)], a non-transformed rat jejunal crypt cell line, were incubated with increasing concentrations of IL-11 (FIG. 2).

IEC-6 cells obtained from the American Type Culture Collection [Rockville, Md.; CRL 1592] were grown in Dulbecco's Modified Eagles Medium [Gibco] with 10% dialyzed fetal calf serum. Cells were studied between passage 20 and 35 by incubating $5 \times 10^4$ cells/well in 96 well plates in media with and without (control) 5–400 ng/ml rhIL-11. After 72 hours incubation, the absorbance of the reduced formazan was measured at 490 nm with an ELISA plate reader using a non-radioactive cell proliferation assay (Cell Titer 96AQ) [Promega, Madison, Wis.] according to the manufacturer's instructions. Samples were done in quadruplicate and samples compared by student t-tests. Results shown are mean +/−S.D. *$p<0.05$.

A dose response was noted when sub-confluent IEC-6 cells were incubated with IL-11, optimal activity occurring at the 50 ng/ml dose. Optimal activity with IL-11 was similar to proliferative activity induced by epidermal growth factor (EGF), a growth factor known to stimulate IEC-6 cells [Baliga et al, *Biochem. Int'l.*, 20, 161–168 (1990)]. No proliferative activity was noted when IL-11 was added to IEC-6 cells after the cells had reached confluence, suggesting there was cycle-specificity to the growth-stimulatory effect of IL-11. Thus, IL-11 has proliferative effects on IEC-6 cells.

Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. A method for enhancing growth of a gut epithelial cell population comprising the step of administering a pharmaceutically effective amount of a cytokine selected from the group consisting of interleukin-11, interleukin-6, leukemia inhibitory factor, oncostatin M, and ciliary neurotrophic factor.

2. The method of claim 1, further comprising administering an additional cytokine.

3. The method of claim 1, wherein said gut epithelial cell population is exposed to chemotherapy or radiation therapy.

4. The method of claim 1, wherein said step of administering said cytokine is before exposure to chemotherapy or radiation therapy.

5. The method of claim 1, wherein said step of administering said cytokine is simultaneously with exposure to chemotherapy or radiation therapy.

6. The method of claim 1, wherein said step of administering said cytokine is subsequent to exposure to chemotherapy or radiation therapy.

7. The method of claim 1, wherein said gut epithelial cell population is exposed to disease or infection.

8. The method of claim 7, wherein said disease is an autoimmune disease selected from the group consisting of Crohn's disease and ulcerative colitis.

9. The method of claim 1, wherein said gut epithelial cell population is exposed to trauma or shock.

10. A method for enhancing growth of a gut epithelial cell population comprising the step of administering a pharmaceutically effective amount of IL-11.

11. A method for enhancing growth of a gut epithelial cell population comprising the step of administering a pharmaceutically effective amount of IL-6.

12. A method for enhancing growth of a small intestinal epithelial cell population comprising the step of administering a pharmaceutically effective amount of a cytokine selected from the group consisting of interleukin-11, interleukin-6, leukemia inhibitory factor, oncostatin M, and ciliary neurotrophic factor.

13. The method of claim 12, further comprising administering an additional cytokine.

14. The method of claim 12, wherein said small intestinal cell population is exposed to chemotherapy or radiation therapy.

15. The method of claim 12, wherein said step of administering said cytokine is before exposure to chemotherapy or radiation therapy.

16. The method of claim 12, wherein said step of administering said cytokine is simultaneously with exposure to chemotherapy or radiation therapy.

17. The method of claim 12, wherein said step of administering said cytokine is subsequent to exposure to chemotherapy or radiation therapy.

18. The method of claim 12, wherein said small intestinal cell population is exposed to disease or infection.

19. The method of claim 18, wherein said disease is an autoimmune disease selected from the group consisting of Crohn's disease and ulcerative colitis.

20. The method of claim 12, wherein said small intestinal cell population is exposed to trauma or shock.

21. A method for enhancing growth of a small intestinal epithelial cell population comprising the step of administering a pharmaceutically effective amount of IL-11.

22. A method for enhancing growth of a small intestinal epithelial cell population comprising the step of administering a pharmaceutically effective amount of IL-6.

23. A method for enhancing growth of a large intestinal epithelial cell population comprising the step of administering a pharmaceutically effective amount of a cytokine selected from the group consisting of interleukin-11, interleukin-6, leukemia inhibitory factor, oncostatin M, and ciliary neurotrophic factor.

24. The method of claim 23, further comprising administering an additional cytokine.

25. The method of claim 23, wherein said large intestinal epithelial cell population is exposed to chemotherapy or radiation therapy.

26. A method for enhancing growth of a large intestinal epithelial cell population comprising the step of administering a pharmaceutically effective amount of IL-11.

27. A method for enhancing growth of a large intestinal epithelial cell population comprising the step of administering a pharmaceutically effective amount of IL-6.

* * * * *